US009517993B2

(12) United States Patent
Yin et al.

(10) Patent No.: US 9,517,993 B2
(45) Date of Patent: Dec. 13, 2016

(54) ANTAGONISTS OF THE TOLL-LIKE RECEPTOR 1/2 COMPLEX

(71) Applicant: THE REGENTS OF THE UNIVERSITY OF COLORADO, a body corporate, Denver, CO (US)

(72) Inventors: Hang Yin, Boulder, CO (US); Kui Cheng, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 3 days.

(21) Appl. No.: 14/417,676

(22) PCT Filed: Jul. 29, 2013

(86) PCT No.: PCT/US2013/052517
§ 371 (c)(1),
(2) Date: Jan. 27, 2015

(87) PCT Pub. No.: WO2014/022287
PCT Pub. Date: Feb. 6, 2014

(65) Prior Publication Data
US 2015/0251987 A1    Sep. 10, 2015

Related U.S. Application Data

(60) Provisional application No. 61/676,992, filed on Jul. 29, 2012.

(51) Int. Cl.
*C07C 49/747*    (2006.01)
*C07C 235/82*    (2006.01)
(Continued)

(52) U.S. Cl.
CPC ........... *C07C 49/747* (2013.01); *C07C 49/755* (2013.01); *C07C 62/38* (2013.01); *C07C 69/21* (2013.01);
(Continued)

(58) Field of Classification Search
None
See application file for complete search history.

(56) References Cited

U.S. PATENT DOCUMENTS

| 2005/0049284 A1* | 3/2005 | Ho ........................ C07C 49/747 514/345 |
| 2006/0147456 A1 | 7/2006 | Lebecque et al. |
| 2011/0123468 A1 | 5/2011 | Wagner et al. |

OTHER PUBLICATIONS

Database CAPLUS Chemical Abstracts Service, Columbus, Ohio, US; Database Accession No. 1950:24913, Abstract of Haworth et al., Journal of the Chemical Society (1949) 3271-8.*
(Continued)

*Primary Examiner* — Karl J Puttlitz
(74) *Attorney, Agent, or Firm* — Sheridan Ross P.C.

(57) ABSTRACT

Provided are compounds, compositions and methods for treating Toll-like receptor 1/2 complex (TLRI/2) related inflammatory disorders. Small molecules, based on the benzotropolone scaffold, capable of influencing downstream signaling are disclosed as well as methods of making and modifying these molecules. Also provided are methods for treating a subject for a clinical condition associated with Toll-like receptor complex 1/2 activation, comprising administering to the subject an effective amount of a benzotropolone compound.

8 Claims, 14 Drawing Sheets

(51) Int. Cl.
*C07C 69/21* (2006.01)
*C07C 69/757* (2006.01)
*C07D 307/93* (2006.01)
*C07C 49/755* (2006.01)
*C07C 62/38* (2006.01)

(52) U.S. Cl.
CPC ............ *C07C 69/757* (2013.01); *C07C 235/82* (2013.01); *C07D 307/93* (2013.01); *C07C 2102/12* (2013.01)

(56) References Cited

OTHER PUBLICATIONS

Database CAPLUS Chemical Abstracts Service, Columbus, Ohio, US; Database Accession No. 1959:39831, Abstract of Cerny, Collection of Czechoslovak Chemical Communications (1958), 24, 24-30.*

Database CAPLUS Chemical Abstracts Service, Columbus, Ohio, US; Database Accession No. 2009:1617713, Abstract of WO 2009156324 BASF Se, Germany, Wagner et al., Dec. 30, 2009.*
Chen et al., Angewandte Chemie, International Edition (2012), 51(49), 12246-12249.*
Cheng et al., "Small Molecule Inhibitors of the TLR3/dsRNA Complex," J. Am. Chem. Soc., 2011, 133(11), pp. 3764-3767.
Hari et al., "Toll-Like Receptors: Role in Dermatological Disease," Hindawi Publishing Corporation, Mediators of Inflammation, 2010, article ID 437246, 16 pages.
Iwaki et al., "The Extracellular Toll-like Receptor 2 Domain Directly Binds Peptidoglycan Derived from *Staphylococcus aureus*," Journal of Biological Chemistry, 2002, 277(27), pp. 24315-24320.
International Search Report and Written Opinion for International (PCT) Patent Application No. PCT/US2013/052517, mailed Dec. 2, 2013, 8 pages.
International Preliminary Report on Patentability for International (PCT) Patent Application No. PCT/US2013/052517, mailed Feb. 3, 2015, 8 pages.

* cited by examiner

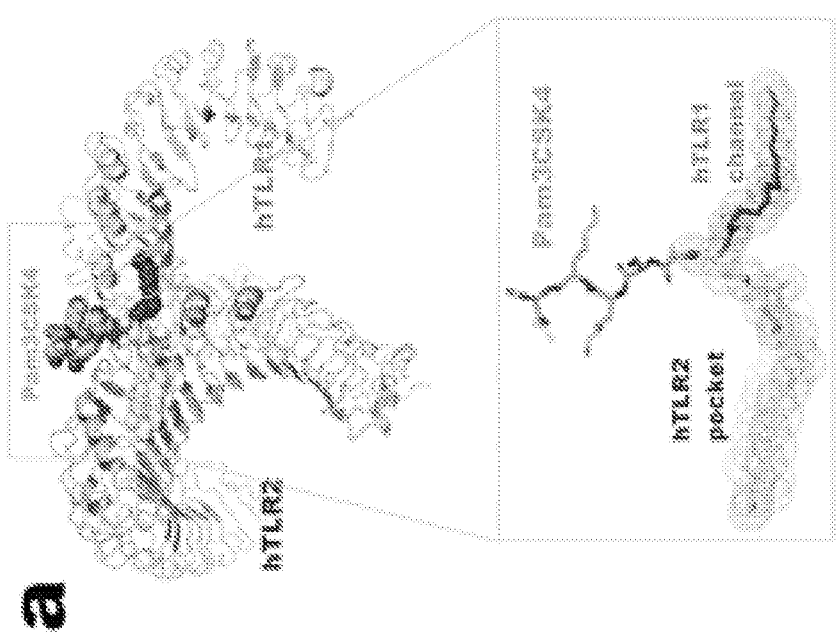
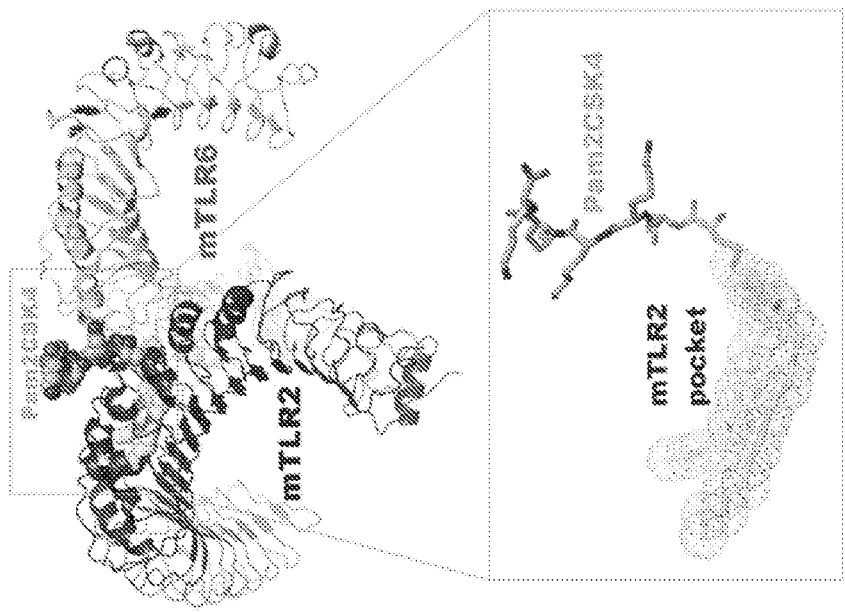
FIGURE 1

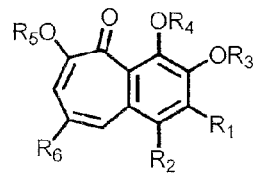

| Compound | R₁ | R₂ | R₃ | R₄ | R₅ | R₆ | IC$_{50}$ (μM) |
|---|---|---|---|---|---|---|---|
| NCI35676 | OH | H | H | H | H | H | 2.45± 0.25 |
| 1 | H | CH₃ | H | H | H | H | 3.13± 0.11 |
| 2 | H | H | H | H | H | H | 2.25± 0.31 |
| 3 | F | H | H | H | H | H | 22.74± 1.37 |
| 4 | OCH₃ | H | H | H | H | H | 4.83± 0.25 |
| 5 | OCH₃ | H | CH₃ | H | CH₃ | H | 11.73± 1.15 |
| 6 | OCH₃ | H | CH₃ | CH₃ | CH₃ | H | 39.91± 0.93 |
| 7 | OCOCH₃ | H | H | H | H | H | 4.83± 0.25 |
| 8 | OCOCH₃ | H | COCH₃ | H | COCH₃ | H | 1.42± 0.21 |
| 9 | OCOCH₃ | H | COCH₃ | COCH₃ | COCH₃ | H | 2.35± 0.41 |
| 10 | OCH₃ | H | H | H | H | COOH | 21.51± 0.43 |
| 11 | OCH₃ | H | H | H | H | COOCH₃ | 3.11± 0.75 |
| 12 | H | H | H | H | H | COOH | 16.49± 0.88 |
| 13 | H | H | H | H | H | CO OCH₃ | 9.01± 0.50 |
| 14 | OCH₃ | H | H | H | H | COOCH₂CH₃ | 2.83± 0.44 |
| 15 | OCH₃ | H | H | H | H | COOCH(CH₃)₂ | 2.47± 0.71 |
| 16 | OCH₃ | H | H | H | H | COO(CH₂)₃CH₃ | 2.83± 0.44 |
| 17(CU-CPT22) | OCH₃ | H | H | H | H | COO(CH₂)₅CH₃ | 0.58± 0.09 |
| 18 | OCH₃ | H | H | H | H | COO(CH₂)₇CH₃ | 0.72± 0.14 |
| 19 | OCH₃ | H | H | H | H | COO(CH₂)₉CH₃ | 1.01± 0.10 |
| 20 | OCH₃ | H | H | H | H | COO(CH₂)₁₃CH₃ | 3.24± 0.13 |
| 21 | OCH₃ | H | H | H | H | CONH(CH₂)₃CH₃ | 1.26± 0.31 |
| 22 | OCH₃ | H | H | H | H | CONH(CH₂)₅CH₃ | 1.36± 0.21 |
| 23 | OCH₃ | H | H | H | H | CH₂OH | 4.11± 0.74 |
| 24 | OCH₃ | H | H | H | H | CONH(o-toluene) | 1.36± 0.21 |

FIGURE 6

ANTAGONISTS OF THE TOLL-LIKE RECEPTOR 1/2 COMPLEX

CROSS REFERENCE TO RELATED APPLICATION

This application is a national stage application under 35 U.S.C. 371 of PCT Application No. PCT/US2013/052517 having an international filing date of Jul. 29, 2013, which designated the United States, which PCT application claimed the benefit of U.S. Application Ser. No. 61/676,992, filed Jul. 29, 2012, both of which are incorporated by reference in their entirety.

GOVERNMENT INTEREST

This invention was made with government support under grant numbers DA026950, DA025740 and NS067425 awarded by the National Institutes of Health. The U.S. government has certain rights in the invention.

FIELD OF THE INVENTION

Embodiments herein report compositions, methods, and uses for treating Toll-like receptor 1/2 complex (TLR1/2) related immune disorders. Some embodiments of the present invention provide small molecules capable of specifically inhibiting TLR1/2, influencing downstream signaling. Other embodiments include methods of generating and/or modifying small molecules useful in the methods and compositions of the invention.

BACKGROUND

The vertebrate immune system is composed of a combination of cells and molecules with specialized roles in defending against infecting pathogens such as bacteria, viruses, fungi, and parasites. There are two fundamentally different types of immune responses to infecting pathogens. Acquired immune responses are mediated by highly specialized, systemic cells which recognize pathogens and generate specific immune responses against them. The acquired immune response provides the vertebrate immune system with the ability to remember specific pathogens, and mount stronger responses upon each repeat pathogen exposure. The generation of acquired immunity takes time however (e.g. 2-3 days post infection), which could leave the body susceptible to the early effects of infection where it not for the innate immune system.

Unlike the acquired immune system, the innate immune system does not confer long-lasting or protective immunity. Rather, the innate immune system provides the body with a first line of defense by recognizing and responding to conserved features of pathogens in a generic way. During an innate immune response, an invading pathogen is recognized by several types of dedicated receptors in the host, including soluble receptors in the blood, and membrane-bound, germline-encoded receptors on the surface of host cells. Stimulation of these membrane-bound receptors, known as Toll-like receptors (TLRs), leads to activation of the transcription factor NF-κB and other signaling molecules that are involved in regulating the expression of cytokine genes, including those encoding TNF-α, IL-1, and certain chemokines.

TLRs are pattern recognition receptors that recognize pathogen-derived macromolecules such as bacterial and yeast cell wall components, and viral and bacterial nucleic acids. The conserved features of pathogens recognized by TLRs are collectively referred to as pathogen-associated molecular patterns (PAMPs). In humans, 11 TLRs respond to a variety of PAMPs, including lipopolysaccharides (TLR4), lipopeptides (TLR2 associated with TLR1 or TLR6), bacterial flagellin (TLR5), viral dsRNA (TLR3), viral or bacterial ssRNA (TLRs 7 and 8), and CpG-rich unmethylated DNA (TLR9), among others.

Because of their ability to initiate and propagate inflammation, TLRs are attractive targets for anti-inflammatory agents. Evidence that TLRs are potential therapeutic targets include overexpression in disease, knockout mice being resistant to disease in disease models, ligands exacerbating inflammation in disease models and genetic differences in TLRs or their signaling proteins correlating with risk of disease. Because TLR activation occurs early in the inflammation cascade, there is potentially an advantage in blocking TLRs.

It has been demonstrated that the cytokine response to human cytomegalovirus (CMV, lymphocytic choriomeningitis virus (LCMV), and herpes simplex virus (HSV-1) is controlled by the TLR1/2 complex. TLR1/2 has been suggested to have beneficial effects in both chronic and acute inflammatory diseases ranging from acne to sepsis, and may also uttenuate pulmonary tumor metastases. While several TLR2 antagonists are currently being developed as therapeutics for cancer and autoimmune disease, these antagonists are all naturally derived. Synthetic low molecular weight compounds with inhibitory activity against TLR 1/2 have not yet been described.

SUMMARY

Some embodiments herein report compositions, methods, and uses for agents capable of binding to and inhibiting activation of TLR1/2.

Some aspects of the invention provide compounds having a benzotropolone moiety within their structure that are capable of attenuating effects of acute inflammatory disease and chronic inflammatory disease.

Another embodiment of the invention provides a reproducible method for synthesizing a compound having a benzotropolone moiety within its structure.

Other aspects of the invention provide methods for treating a subject for a clinical condition associated with Toll-like receptor complex 1/2 activation. Such treatment methods typically include administering to the subject a compound of the invention.

In some embodiments, the clinical condition comprises a chronic inflammatory disease or an acute inflammatory disease. Within these embodiments, in some instances, the clinical condition comprises a clinical condition associated with viral infection, atopic dermatitis, psoriasis, acne, or sepsis. While clinical conditions associated with a wide variety of viral infections can be treated by methods of the invention, in some particular cases, methods of the invention are used to treat a chronic inflammatory disease or an acute inflammatory disease caused by human cytomegalovirus, lymphocytic choriomeningitis, herpes simplex virus 1, or a combination thereof. Yet other aspects of the invention provide methods for treating pulmonary tumor metastases.

The benzotropolone-containing compounds of the present invention can be made in forms suitable for oral delivery. The benzotropolone-containing compounds of the present invention can be administered to maintain a blood concentration sufficient to allow the manifestation of pharmacological effect.

BRIEF DESCRIPTION OF THE DRAWINGS

FIG. 1. FIG. 1a shows the crystal structure of TLR1/TLR2/Pam3CSK4 (Protein Data Bank (PBD) ID 2Z7X). The Pam3CSK4-binding pocket in the hTLR1-TLR2 complex is amplified in the lower box. FIG. 1b shows the crystal structure of TLR2/TLR6/Pam$_2$CSK$_4$. The Pam2CSK4-binding pocket in the mTLR2 complex is amplified in the lower box.

FIG. 2a shows a bright field image of Hi 5 cells. The cells exhibited fluorescence after 3 days incubation with recombinant virus. FIG. 2b shows the TLR2 protein after purification, as observed by coomassie brilliant blue stain.

FIG. 3a shows the viability and FIG. 3b shows the inhibitory activity of the nine initial hits from the NCI-diversity small-molecule library at 3 μM. The nine compounds can inhibit 70% TLR1/2 signaling with no significant toxicity issues as determined by nitric oxide (NO) and MTT assay, respectively.

FIG. 4a shows that NCI35676 exhibited a half-maximal inhibitory concentration (IC50) of 2.45±0.25 μM as observed by nitric oxide (NO) assay. FIG. 4b shows the specificity test for NCI35676 (3 μM) with TLR-specific agonists:

TLR3: 15 μg/mL Poly (I:C),

TLR4: 10 ng/mL LP S,

TLR1/2: 200 ng/mL Pam3CSK4,

TLR2/6: 10 ng/mL FSL-1, and

TLR7: 100 nM R848 was used to selectively respective TLRs.

Figure 5:
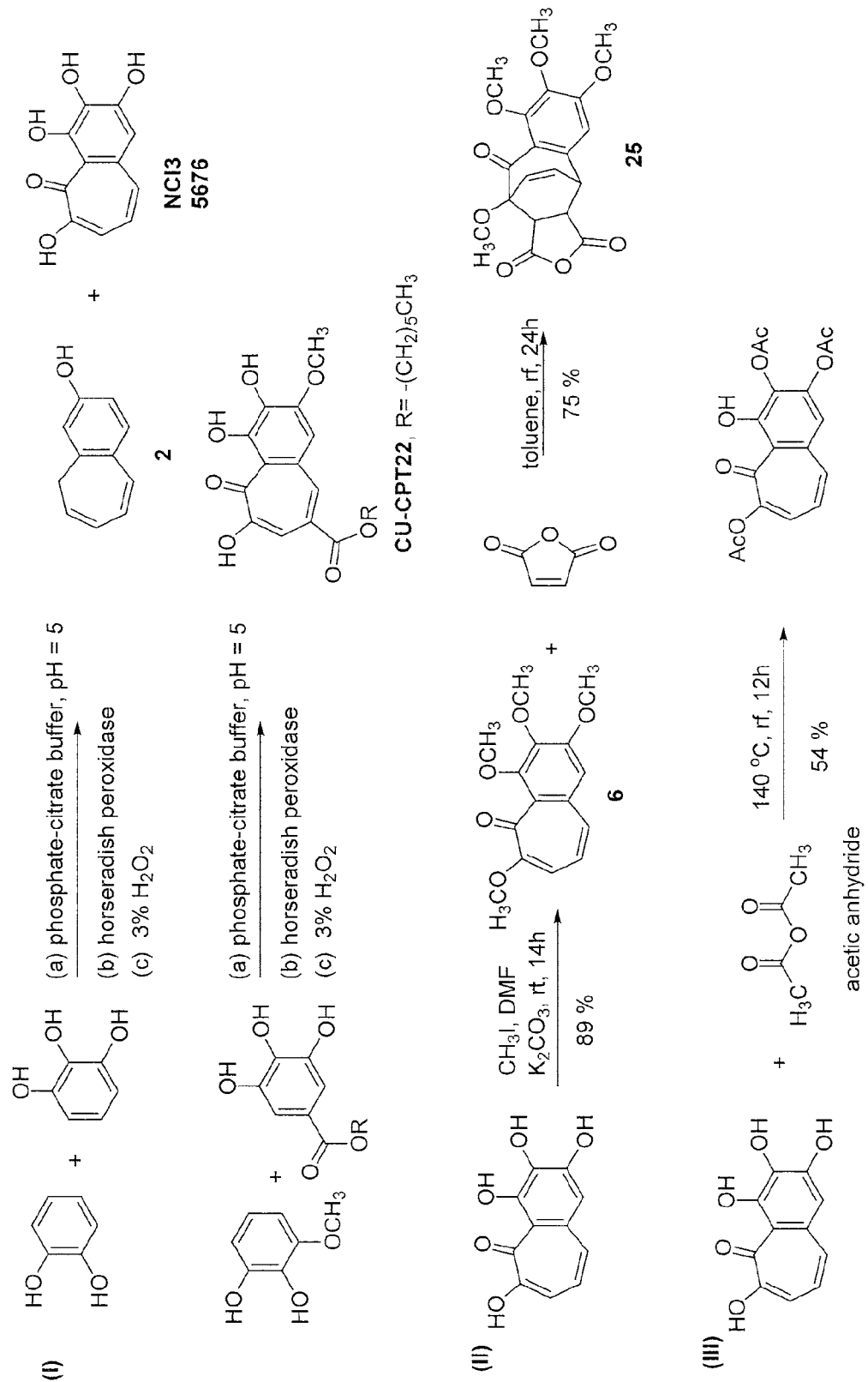
Figure 5:
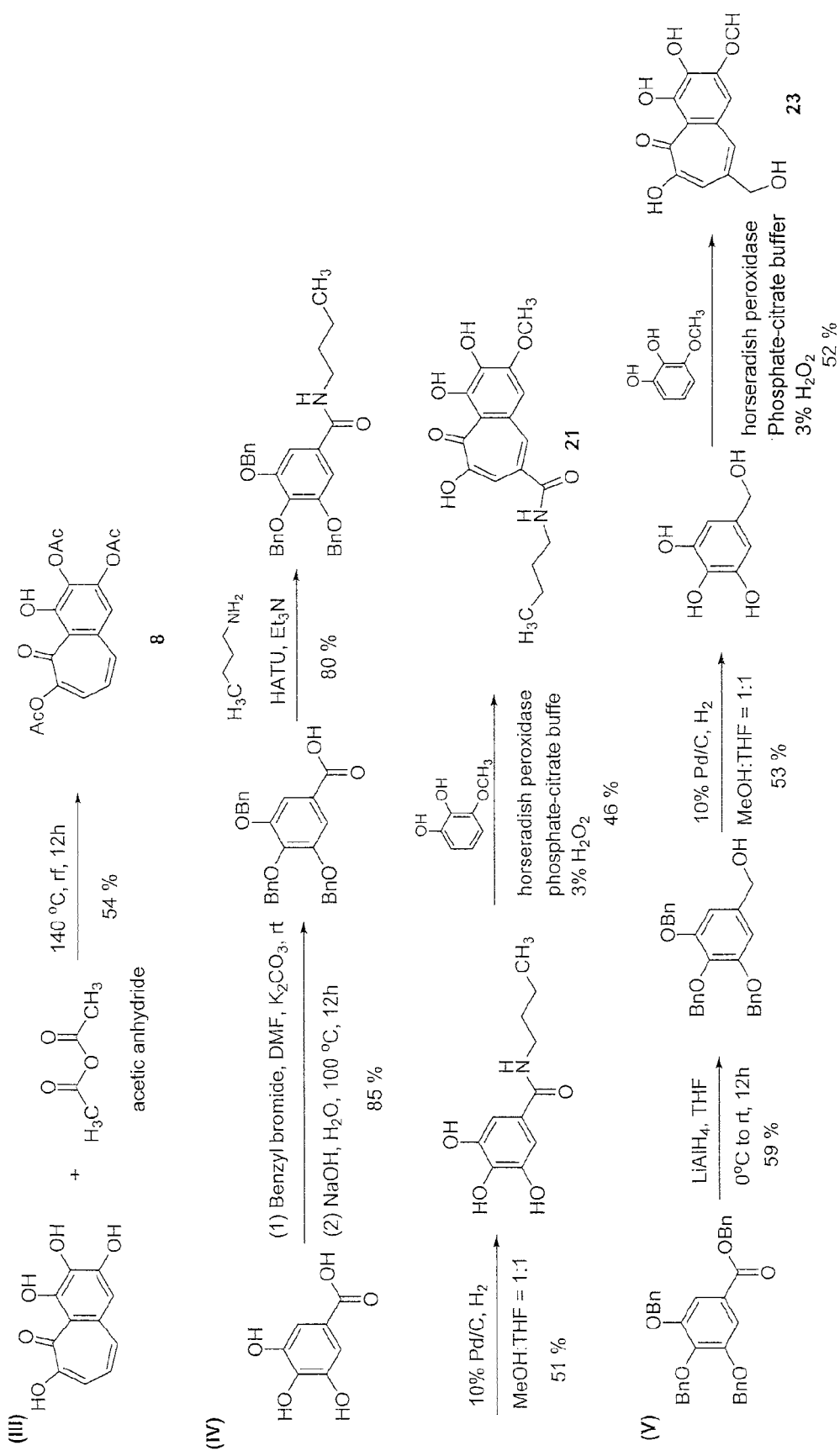
Figure 7A:
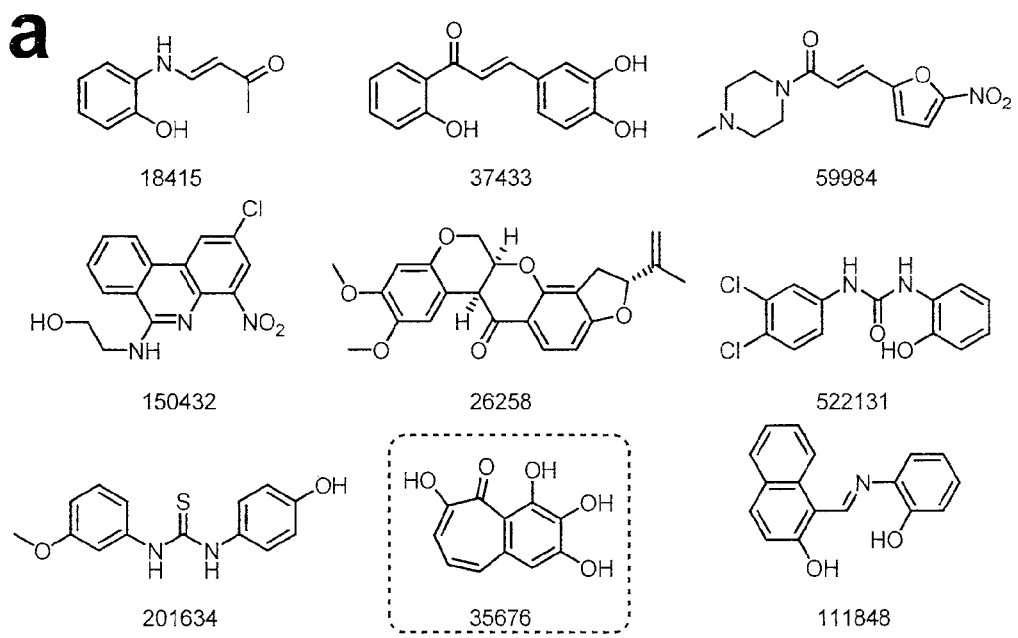
Figure 7B:
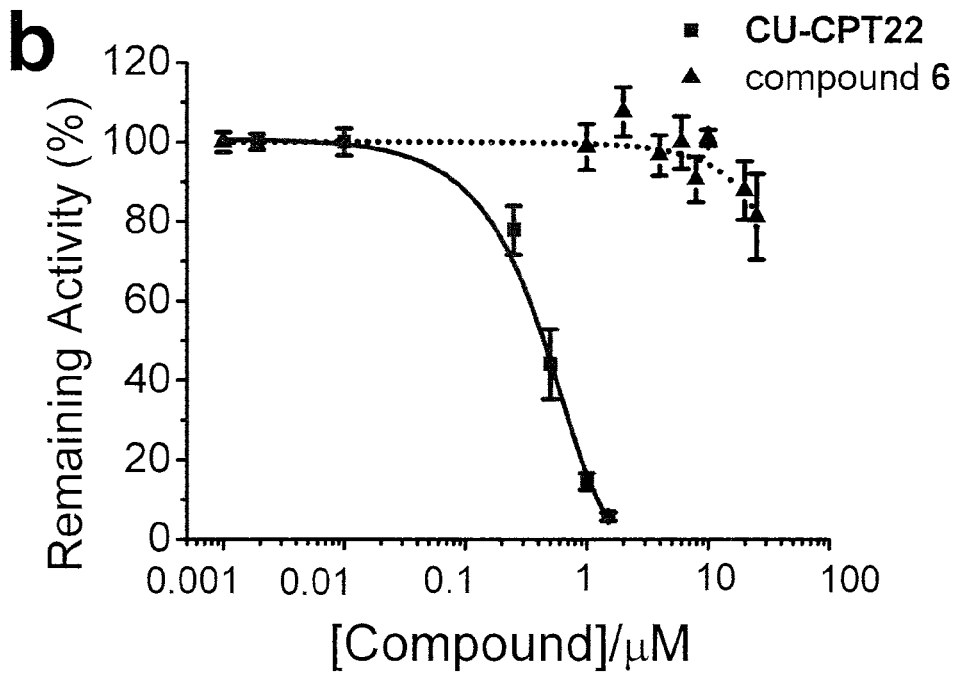
Figure 7C:
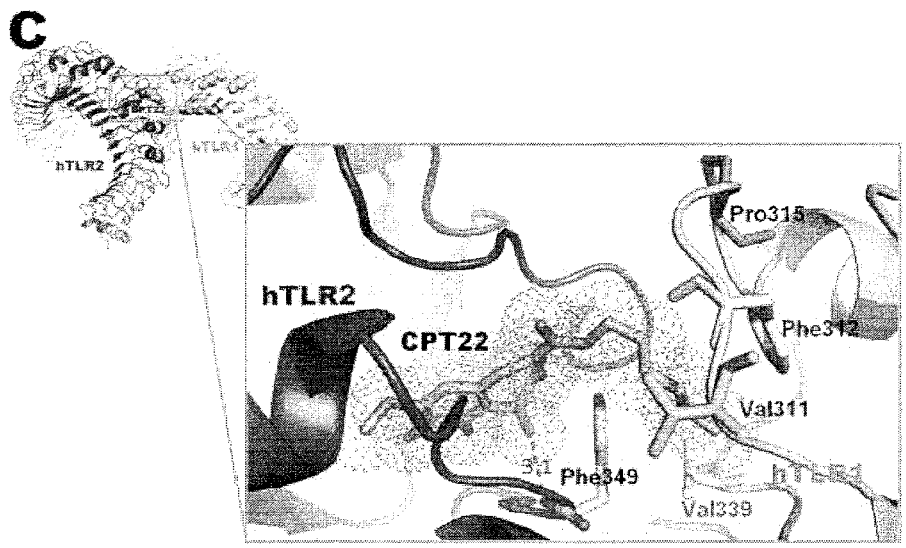
Figure 7D:
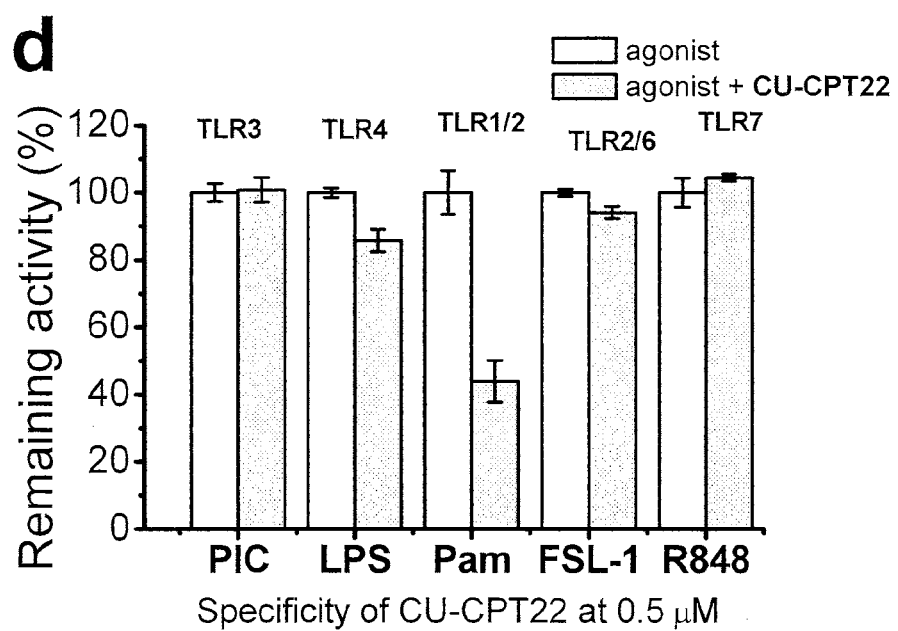
Figure 8A:
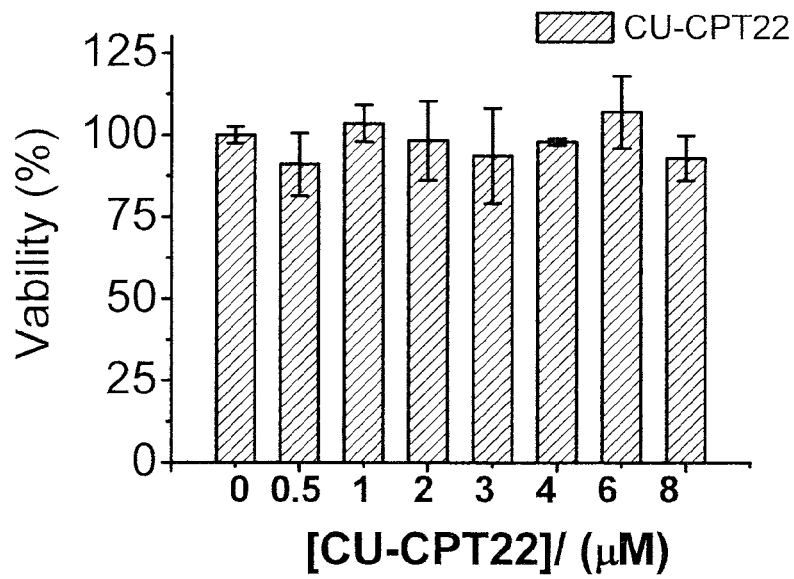
Figure 8B:
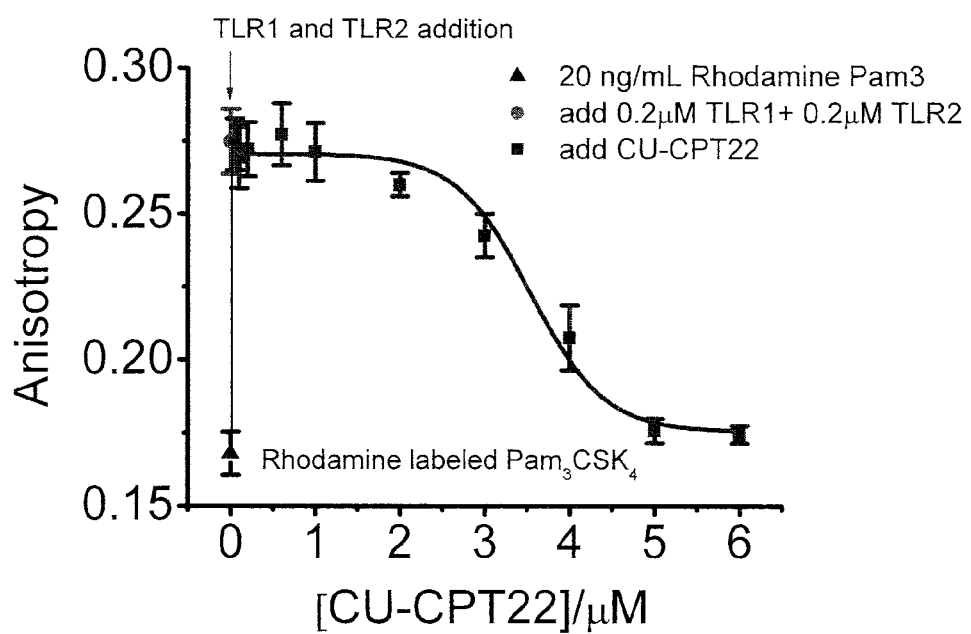
Figure 8C:
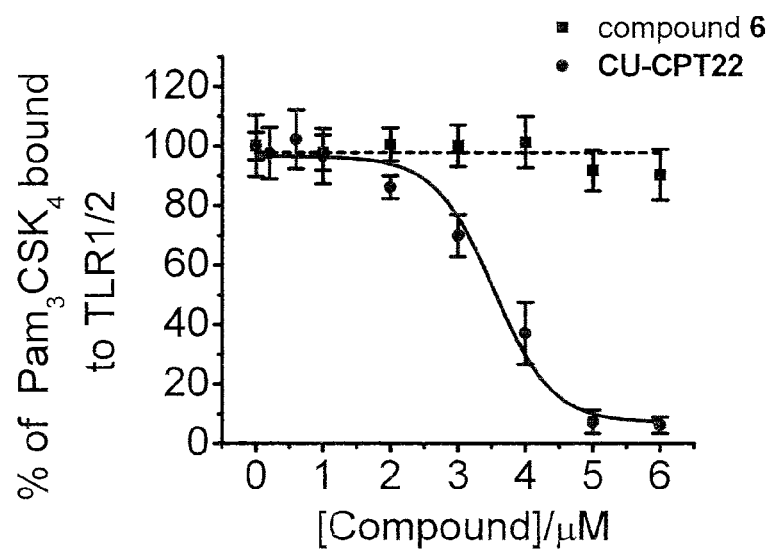
Figure 8D:
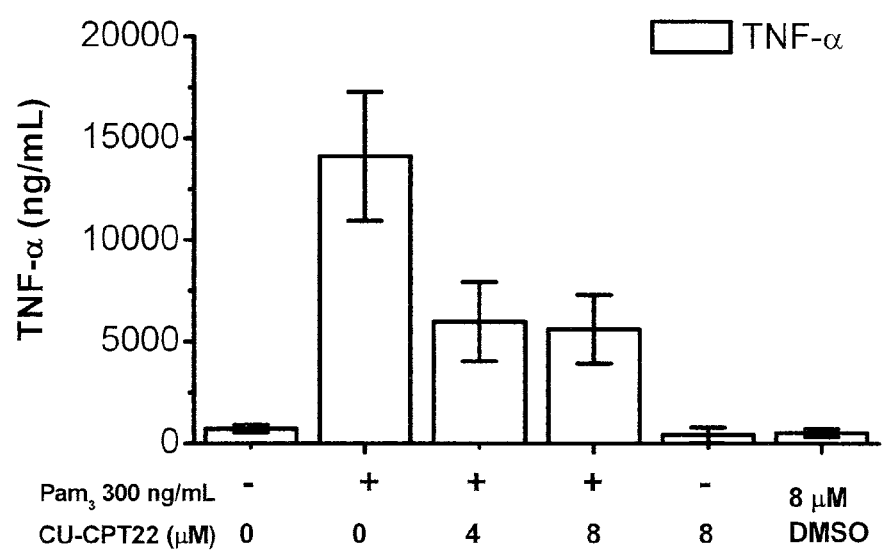
Figure 8E:
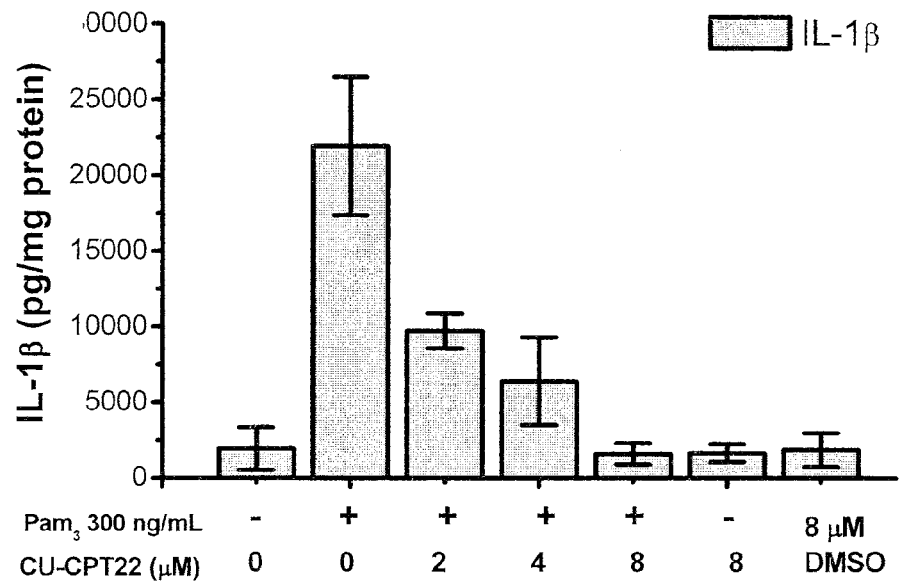

FIG. 5. Representative synthesis of TLR1/2 inhibitors. A series of NCI35676 analogs were designed around the benzotropolone scaffold and synthesized using a one-pot reaction with sequential addition of phosphate-citrate buffer (pH=5), horseradish peroxidase, and 3% hydrogen peroxide.

FIG. 6. Structure-activity relationship Of the synthesized benzotropolone analogs in RAW 264.7 cells. IC$_{50}$ and corresponding SD values (in μM) are averages determined from the results of at least three independent repeats. Additional compound activity was determined for the following structures:

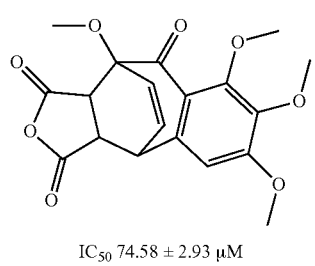

Compound 25

IC$_{50}$ 74.58 ± 2.93 μM

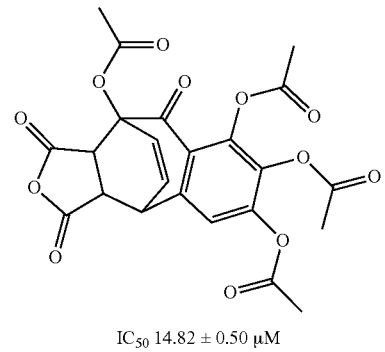

Compound 26

IC$_{50}$ 14.82 ± 0.50 μM

FIG. 7. Screened result and the identification of CU-CPT22 (compound 17). FIG. 7a shows the nine top initial hits from the NCI-diversity small-molecule library, which can inhibit TLR1/2 at least 70% at a concentration of 3.0 μM. FIG. 7b shows dose-dependent inhibitory activity of CU-CPT22 with the negative control compound 6. FIG. 7c shows a binding site prediction of CU-CPT22 to TLR1/2 performed by Glide 5.6 (Shrodinger Inc. Oregon). The six-membered carbon chain fit well into the hydrophobic channel of hTLR1, having key hydrophobic interactions with Val311, Phe312, Pro315, and Val339. FIG. 7d shows a specificity test for CU-CPT22 (0.5 μM) with various TLR-specific agonists: TLR3: 15 μg/mL Poly (I:C), TLR4: 10 ng/mL LPS, TLR1/2: 200 ng/mL Pam3CSK4, TLR2/6: 10 ng/mL FSL-1, and TLR7: 100 nM R848 were used to selectively respective TLRs.

FIG. 8. Viability, biophysical evaluation, and downstream signaling with CU-CPT22. FIG. 8a demonstrates viability: no significant toxicity issues were detected under 8 μM by MIT assay. FIG. 8b shows the fluorescence anisotropy assay showed competitive binding between CU-CPT22 and Pam3CSK4 for TLR1/2. Inhibition curve was fitted using a one-site competition model. FIG. 8c shows normalized binding of CU-CPT22 compared with the negative control, compound 6. FIG. 8d shows the ELISA assay results demonstrating TNF-α inhibition by CU-CPT22, and FIG. 8e shows IL-1β production activated by 300 ng/mL Pam3CSK4 is inhibited by CU-CPT22.

Figure 9:
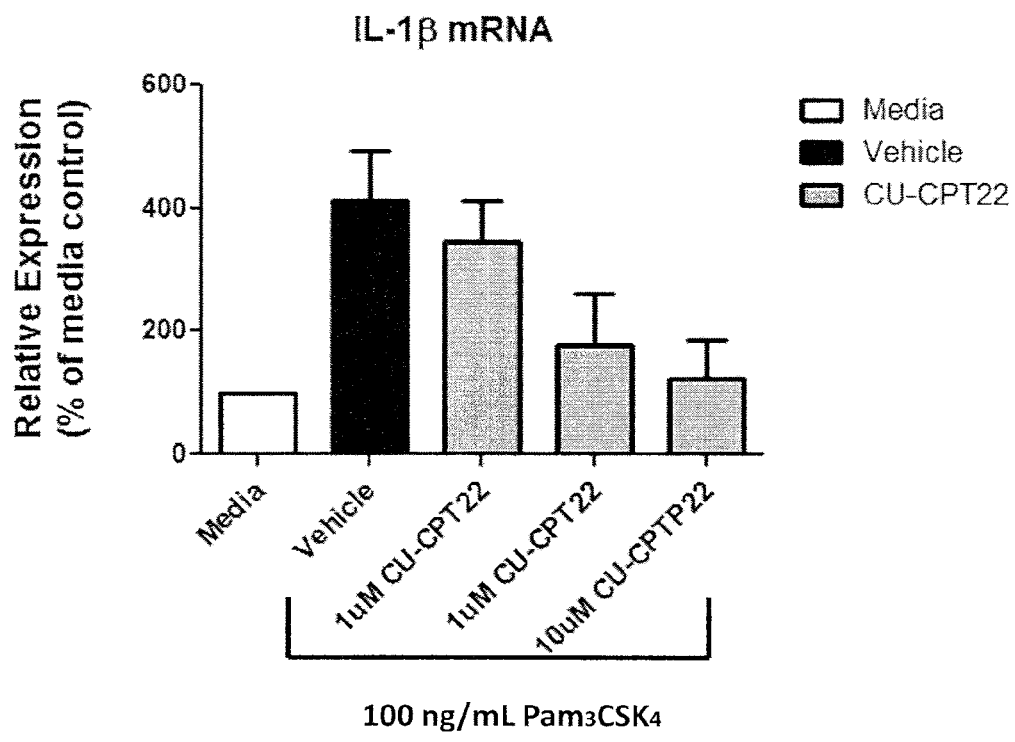

FIG. 9. Dose-dependent inhibition of IL-1β by CU-CPT22 in isolated microglial cells incubated with Pam3CSK4 and CU-CPT22 for 2 hours (N=4).

Figure 10A:
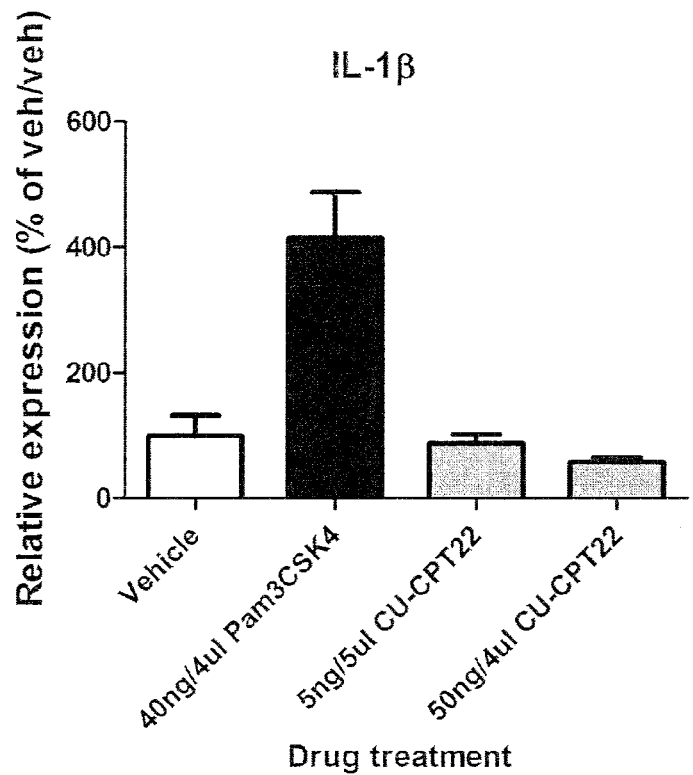
Figure 10B:
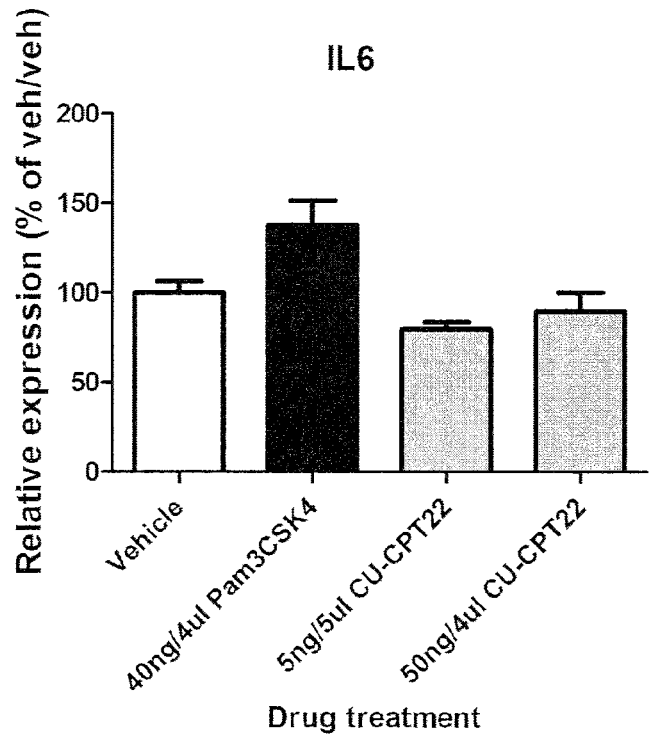
Figure 10C:
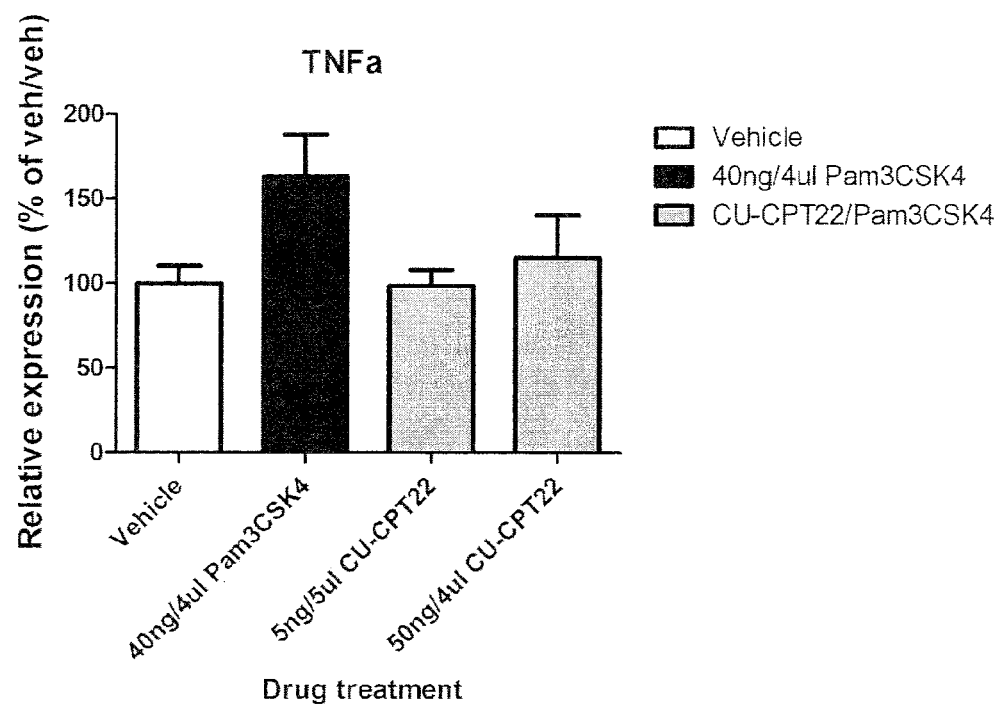

FIG. 10. In vivo administration of Pam3CSK4 and CU-CPTP22 ICM. CU-CPT22 shows strong inhibition of IL-10 mRNA expression (FIG. 10a), TNF-α mRNA expression (FIG. 10b) and IL-6 mRNA expression (FIG. 10c) in hippocampal tissue taken 2 hours after injection.

DETAILED DESCRIPTION OF THE INVENTION

Definitions

"Alkyl" refers to a saturated linear monovalent hydrocarbon moiety of on to twenty, typically one to twelve, and often one to six, carbon atoms or a saturated branched monovalent hydrocarbon moiety of three to twenty, typically three to twelve, and often three to six, carbon atoms. Exemplary alkyl groups include, but are not limited to, methyl, ethyl, n-propyl, 2-propyl, tert-butyl, pentyl, and the like.

"Halide" refers to fluorine, chlorine, bromine, or iodine.

"Pharmaceutically acceptable excipient" refers to an excipient that is useful in preparing a pharmaceutical composition that is generally safe, non-toxic, and neither biologically nor otherwise undesirable, and includes excipients that are acceptable for veterinary uses as well as human pharmaceutical use.

"Pharmaceutically acceptable salt" of a compound means a salt that is pharmaceutically acceptable and that possesses the desired pharmacological activity of the parent compound.

"Phenyl group" refers to a group comprising the univalent organic radical $C_6H_5$, which forms an aromatic six-membered hexagonal planar ring.

The terms "pro-drug" and "prodrug" are used interchangeably herein, and refer to a pharmacologically substantially inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple, etc., depending on the number of biotransformation steps required to release the active drug within the organism, and indicating the number of functionalities present in a precursor-type form. Prodrug forms often offer advantages of solubility, tissue compatibility, or delayed release in the mammalian organism. Prodrugs commonly known in the art include acid derivatives that are well known to one skilled in the art, such as, but not limited to, esters prepared by reaction of the parent acid compound with an amine, or basic groups reacted to form an acylated base derivative. Moreover, the prodrug derivatives of this invention may be combined with other features herein taught to enhance bioavailability.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the subject to be treated.

"Treating" or "treatment" of a disease includes: 1) preventing the disease, i.e. causing the clinical symptoms of the disease not to develop in a subject that may be exposed to or predisposed to the disease but does not yet experience or display symptoms of the disease; 2) inhibiting the disease, i.e. arresting or reducing the development of the disease or its clinical symptoms; or 3) relieving the disease, i.e. causing regression of the disease or its clinical symptoms.

Compounds of the Invention

Some embodiments of the invention provide compounds of the structure:

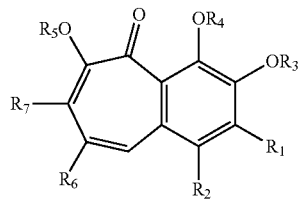

wherein
$R_1$ is —H, —$OR_8$, —$OCOR_8$, —$OSO_2R_9$;
$R_2$ is —H, $CH_3$, or a halide;
$R_3$ is —H, —$COCH_3$, or $R_8$;
$R_4$ is —H, —$COCH_3$, or $R_8$;
$R_5$ is —H, —$COCH_3$, or $R_8$;
$R_6$ is —H, —$COOCH(CH_3)_2$, —$COO(CH_2)_nCH_3$ where n is 3, 5, 7, 9, or 13, —$CH_2OH$, —$CONHR_8$, or —$CONHR_8$;
$R_7$ is —H, or $R_8$;
$R_8$ is an alkyl group; and,
$R_9$ is phenyl;
or a pharmaceutically acceptable salt thereof.

Within these embodiments, in some instances $R_1$ is —$OR_8$, where $R_8$ is a $C_1$-$C_{12}$ alkyl group. In some instances, $R_1$ is more preferably a methoxy group. In yet other instances, $R_1$ is hydrogen, or —$OCOR_8$ where $R_8$ is a $C_1$-$C_{12}$ alkyl group, or —$OSO_2R_9$ where $R_9$ is phenyl. In other instances, $R_2$ is hydrogen, methyl, or a halide chosen from one of fluorine, chlorine, bromine, or iodine. In other instances $R_3$, $R_4$, and $R_5$ are hydrogen, acetyl, or an alkyl group. In other instances, $R_2$, $R_3$, $R_4$, and $R_5$ are hydrogen. In other instances, $R_6$ is hydrogen, —$COOCH(CH_3)_2$, or —$COO(CH_2)_nCH_3$ where n is 3, 5, 7, 9, or 13, —$CH_2OH$, —$CONHR_8$, or —$CONHR_8$, where $R_8$ is an alkyl group and $R_9$ is phenyl. In some instances, n is 3, 5, or 7. In other embodiments, $R_7$ is hydrogen or alkyl (e.g. methyl, ethyl, isopropyl, isobutyl, isopentyl, etc.)

It should be appreciated that combinations of the various embodiments and instances described herein form other embodiments. For example, in one particular embodiment $R_1$ is methoxy, $R_2$ $R_3$, $R_4$, and $R_5$ are hydrogen, $R_6$ is $COO(CH_2)_5CH_3$, and $R_7$ is hydrogen. In this manner, a variety of compounds are embodied within the present invention.

Representative compounds of the invention include, but are not limited to those shown in Table 1 below.

TABLE 1

Representative Compounds of the Invention

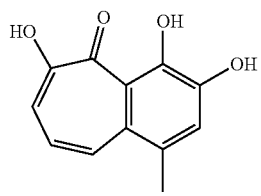 [SMILES: Cc1cc(O)c(O)c2c(=O)c(O)cccc12]

1

TABLE 1-continued

Representative Compounds of the Invention

| Structure | No. |
|---|---|
| (benzo-fused cycloheptanone with HO, O, OH, OH, OH substituents) | 2 |
| (benzo-fused cycloheptanone with HO, O, OH, OH, F substituents) | 3 |
| (benzo-fused cycloheptanone with HO, O, OH, OH, OMe substituents) | 4 |
| (benzo-fused cycloheptanone with MeO, O, OH, OMe, OMe substituents) | 5 |
| (benzo-fused cycloheptanone with MeO, O, OMe, OMe, OMe substituents) | 6 |
| (benzo-fused cycloheptanone with HO, O, OH, OH, OAc substituents) | 7 |
| (benzo-fused cycloheptanone with AcO, O, OH, OAc, OAc substituents) | 8 |

TABLE 1-continued
Representative Compounds of the Invention
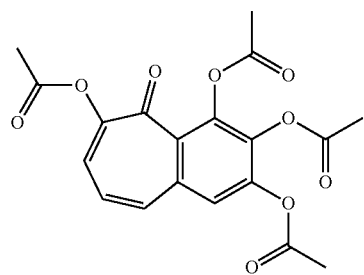 [SMILES: CC(=O)Oc1cc2cccc(OC(C)=O)c(=O)c2c(OC(C)=O)c1OC(C)=O]
9
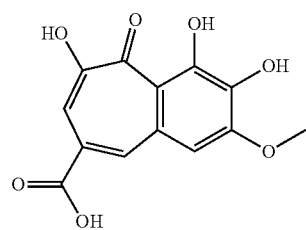 [SMILES: COc1cc2cc(C(=O)O)cc(O)c(=O)c2c(O)c1O]
10
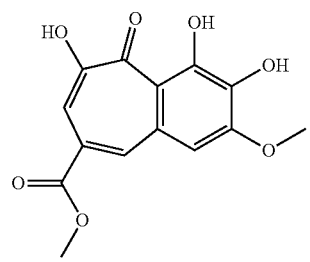 [SMILES: COC(=O)c1cc(O)c(=O)c2c(O)c(O)c(OC)cc2c1]
11
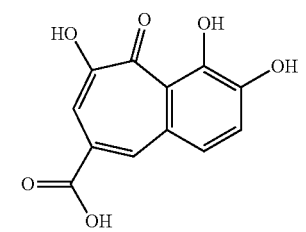
12
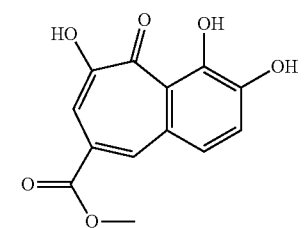 [SMILES: COC(=O)c1cc(O)c(=O)c2c(O)c(O)ccc2c1]
13
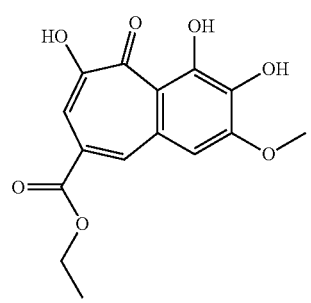 [SMILES: CCOC(=O)c1cc(O)c(=O)c2c(O)c(O)c(OC)cc2c1]
14

TABLE 1-continued
Representative Compounds of the Invention
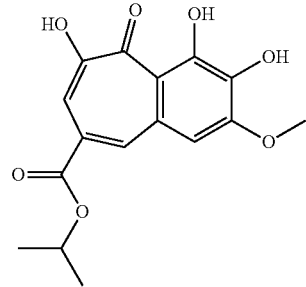 [SMILES: COc1cc2cc(C(=O)OC(C)C)cc(O)c(=O)c2c(O)c1O]
15
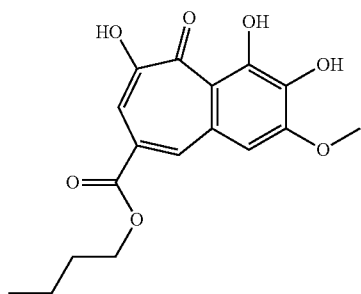 [SMILES: CCCCOC(=O)c1cc(O)c(=O)c2c(O)c(O)c(OC)cc2c1]
16
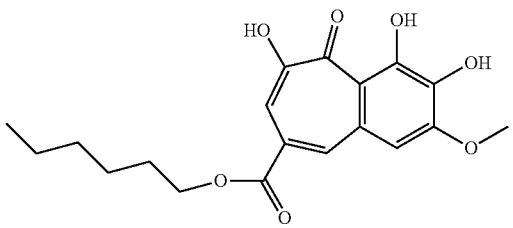 [SMILES: CCCCCCOC(=O)c1cc(O)c(=O)c2c(O)c(O)c(OC)cc2c1]
17
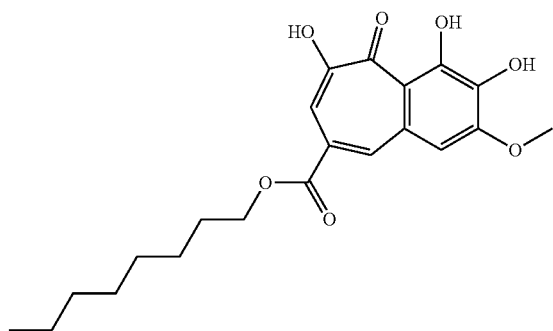 [SMILES: CCCCCCCCOC(=O)c1cc(O)c(=O)c2c(O)c(O)c(OC)cc2c1]
18
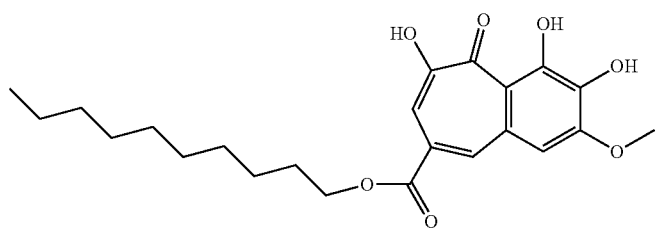 [SMILES: CCCCCCCCCCOC(=O)c1cc(O)c(=O)c2c(O)c(O)c(OC)cc2c1]
19

TABLE 1-continued
Representative Compounds of the Invention
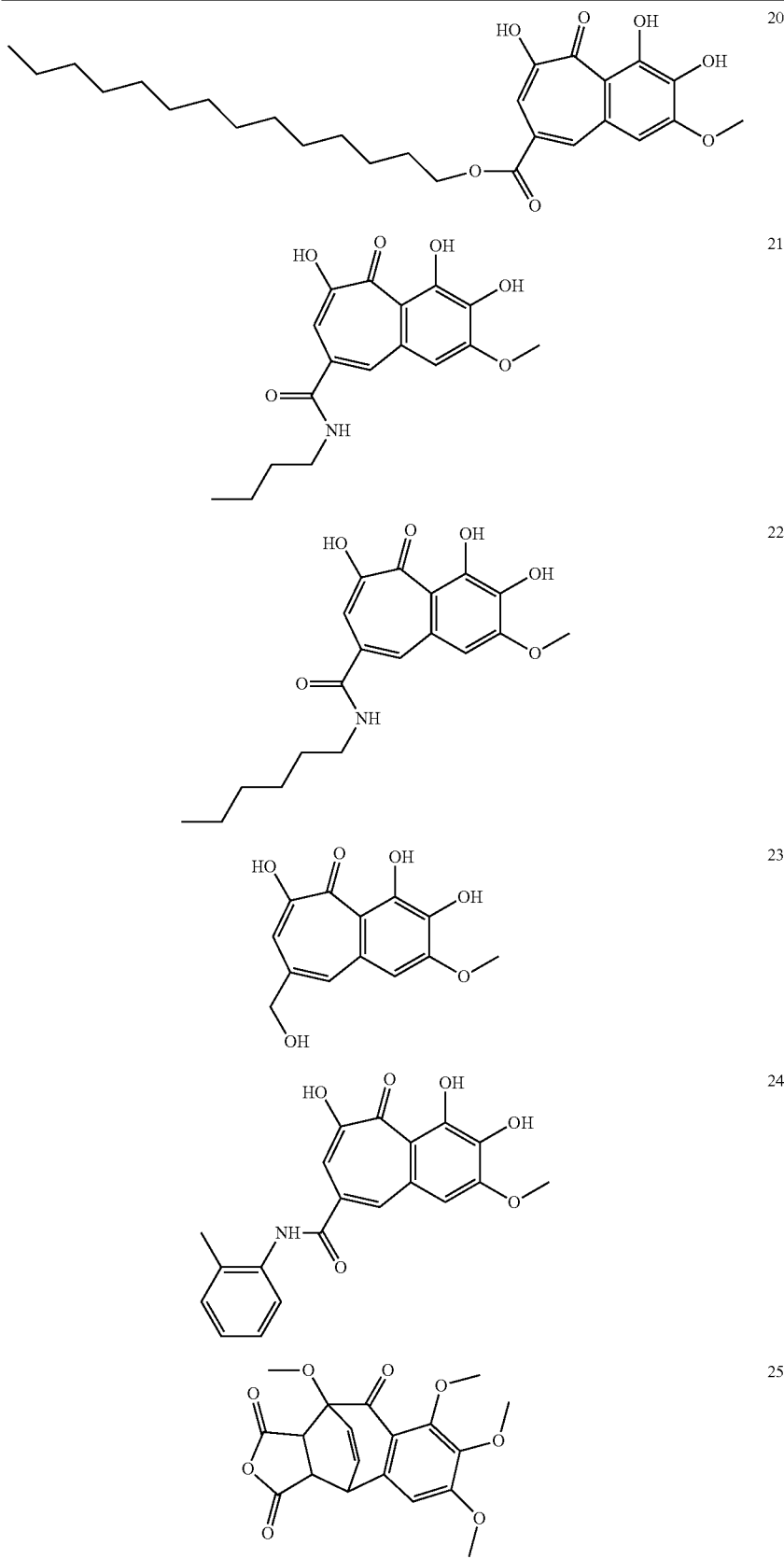

TABLE 1-continued

Representative Compounds of the Invention

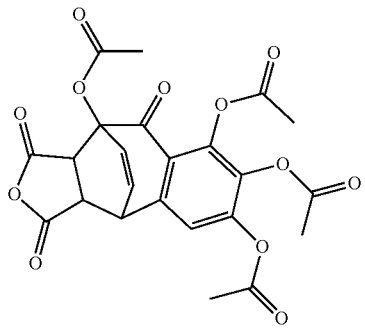 [SMILES: CC(=O)Oc1cc2c(c(OC(C)=O)c1OC(C)=O)C(=O)C1(OC(C)=O)C=CC2C2C(=O)OC(=O)C21]

26

Synthesis

The compounds of the present invention can be synthesized from readily available starting materials. Various substituents on the compounds of the present invention can be present in the starting compounds or added to any one of the intermediates by known methods of substitution or conversion reactions. Because the compounds of the present invention can have certain substituents which are necessarily present, the introduction of each substituent is dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the ring involved.

If the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H Wilen; John Wiley & Sons, Inc., New York, 1981, which are herein incorporated by reference in their entirety. The resolution of compounds is based on the differences in the physical properties of diastereomers by attachment, either chemically or enzymatically, of an enantiomerically pure moiety results in forms that are separable by fractional crystallization, distillation, or chromatography.

It is to be understood that the scope of this invention encompasses not only the various isomers which may exist, but also the various mixtures of isomers which may be formed.

In some aspects of the invention, NCI35676 analogs were designed around the benzotropolone scaffold using known synthetic methods. See Kerschensteiner et al., *Crocipodin, a benzotropolone pigment from the mushroom Leccinum crocipodium (Boletales)*, Tetrahedron (20110), 67:1536-39, which is herein incorporated by reference in its entirety. Generally, compounds of the invention are synthesized in a one-pot reaction with the sequential addition of (a) phosphate-citrate buffer (pH=5), (b) horseradish peroxidase, and (c) 3% hydrogen peroxide. This method provides a concise general synthetic route that can afford the benzotropolone derivative with a yield in the range of 15-60%.

In still other aspects of the invention, the compounds of the invention are in the form of a pharmaceutically acceptable salt.

A more detailed example of synthesizing compounds of the invention is provided in the Examples section below with reference to FIG. 5.

Methods of Use

Compounds of the invention are Toll-like receptor 1/2 complex (TLR1/2) inhibitors. Compounds of the invention and compositions comprising a compound of the invention are useful in treating clinical conditions associated with acute inflammatory and chronic inflammatory diseases. In some instances, the clinical condition comprises, but is not limited to, a clinical condition associated with viral infection, atopic dermatitis, psoriasis, acne, or sepsis. While clinical conditions associated with a wide variety of viral infections can be treated by methods of the invention, in particular instances, methods of the invention are used to treat a chronic inflammatory disease or an acute inflammatory disease caused by human cytomegalovirus, lymphocytic choriomeningitis, herpes simplex virus 1, or a combination thereof. TLR1/2 antagonists of this disclosure may also be beneficial in attenuating metastases of pulmonary tumor(s). Other clinical conditions associated with stimulation of TLR1/2, which are known to one skilled in the art, may also be treated by compounds of the invention.

Atopic dermatitis or eczema is an inflammatory skin disease that is associated with a hereditary predisposition to atopic conditions, which include allergic rhinitis, allergic keratoconjuntivitis, asthma, and eczema (Nat. Rev. Immunol. 2004, 4, 211-222).

Psoriasis is an inflammatory skin disease that is characterized clinically by cutaneous erythematous plaques with thick slivery scale (Nat. Rev. Immunol. 2004, 4, 211-222). Interestingly, a previous report demonstrated that topical application of the TLR7 agonist imiquimod induced the spreading of a psoriatic plaque (Microbes Infect. 2000, 2, 933-943). Thus, TLR activation may also play a role in the pathophysiology of psoriasis by exacerbating the disease process.

Acne vulgaris is an inflammatory skin disease that occurs mostly during adolescence and involves inflammation of the pilosebaceous unit. The anerobic bacterium *Propionibacterium acnes* has been associated with the inflammation in acne lesions. Kim et al. demonstrated that TLR2 on human monocytes can be activated by *P. acnes* in vitro, resulting in increased production of IL-12 and IL-8 (J. Immunol. 2002, 169, 1535-1541). Furthermore, macrophages expressing TLR2 were found surrounding pilosebaceous units of histologic sections of acne lesions from patients (J. Immunol. 2002, 169, 1535-1541). Interestingly, topical retinoids such as all-trans retinoic acid and adapalene, which are used clinically to treat acne, have been shown to decrease TLR2 expression (J. Immunol. 2005, 174, 2467-2470). Tenaud et al. demonstrated that adapalene can decrease TLR2 expression on epidermal keratinocytes of explants of normal human skin and explants of acne lesions (Exp. Dermatol. 2007, 16, 500-506.). Thus, TLR2 has been implicated in the inflammatory process in acne *vulgaris* and topical retinoids may help decrease the inflammation in acne lesions by decreasing expression and function of TLR2 (Adv Dermatol. 2008, 24, 71-87).

The compounds of the present invention can be administered to a subject to achieve a desired physiological effect. Typically the subject is an animal, often a mammal, and more often a human. The compound can be administered in a variety of forms adapted to the chosen route of administration, i.e., orally or parenterally. Parenteral administration in this respect includes, but is not limited to, the following routes: intravenous; intramuscular; subcutaneous, transepithelially, dermal, and rectal systemic.

The active compound can be orally administered, for example, with an inert diluent or with an assimilable edible carrier, or it can be enclosed in hard or soft shell gelatin capsules, or it can be compressed into tablets. For oral therapeutic administration, the active compound may be incorporated with excipient and used in the form of ingestible tablets, buccal tablets, troches, capsules, elixirs, suspensions, syrups, wafers, and the like. Such compositions and preparations can contain at least 0.1% of active compound. The amount of active compound in such therapeutically useful compositions is such that a suitable dosage will be obtained.

It will be recognized by one skilled in the art that a compound of the invention can be incorporated into sustained-release preparations and formulations. The compounds of the present invention may be administered by controlled release means and/or delivery devices capable of releasing the active ingredient (TLR1/2 inhibitor) at the required rate to maintain constant pharmacological activity for a desired period of time. Such dosage forms provide a supply of a drug to the body during a predetermined period of time and thus maintain drug levels in the therapeutic range for longer periods of time than conventional non-controlled formulations It will also be recognized by one skilled in the art that a compound of the invention can be formulated as a prodrug. In a prodrug formulation, a compound of the invention is present in a substantially inactive derivative form that requires biotransformation, either spontaneous or enzymatic, within the organism to release the active drug. Prodrugs become the compounds of the invention which are pharmaceutically active in vivo when they undergo solvolysis under physiological conditions or undergo enzymatic degradation.

The therapeutic compounds of the present invention can be administered to a mammal alone or with pharmaceutically acceptable carriers with pharmaceutically acceptable carriers, the proportion of which is determined by the solubility and chemical nature of the compound, chosen route of administration, and standard pharmaceutical practice.

The physician will determine the dosage of the present therapeutic agents which will be most suitable for prophylaxis or treatment and it will vary with the form of administration and the particular compound chosen, and with the particular patient under treatment. The physician will generally wish to initiate treatment with small dosages by small increments until the optimum effect under the circumstances is reached, where a therapeutically effective amount has been determined. The therapeutic dosage can generally be from about 0.1 to about 1000 mg/day, and or from 0.1 to about 50 mg/Kg of bodyweight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting or exhaustive.

EXAMPLES

Identification of Inhibitors by Cell-Based Screening

To identify novel TLR1/2 complex inhibitors, a cell-based assay was employed to screen the NCI-2 diversity small-molecule library. This 1,363 compound library was chosen from the larger NCI library, which has more than 140,000 compounds, on the basis of availability, purity, and other pharmacological features, such as relative rigidity, number of rotatable bonds and chiral centers, the absence of obvious leaving groups and weakly bounded heteroatoms, etc. Screening was performed in a 96-well plate format using a previously established high-throughput nitric oxide (NO) assay. See e.g. Cheng et al., *Small molecule inhibitors of the TLR3/dsRNA complex*, J. Am. Chem. Soc. (2011), 133:3764-67, which is herein incorporated by reference in its entirety. Briefly, synthetic triacylated lipoprotein Pam3CSK4 was employed to selectively activate TLR1/2 signaling, resulting in the expression of inducible nitric oxide synthase (iNOS) and the production of NO in RAW 264.7 macrophage cells. NO levels were monitored as an indicator of Pam3CSK4-induced TLR1/2 activation to evaluate the compound's inhibitory activity.

Figure 2:
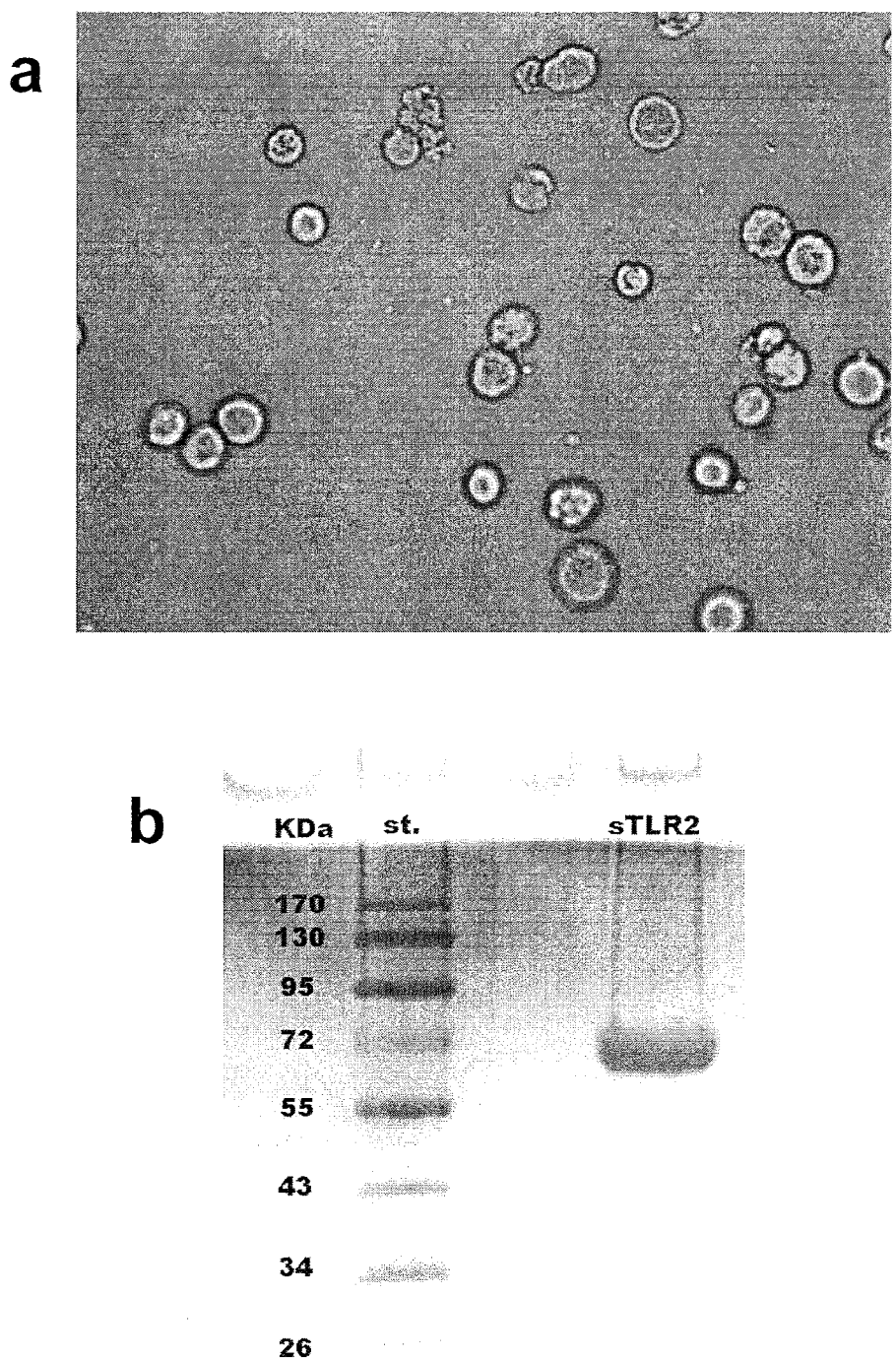
FIG. 2. Characterization of prepared human TLR2 (his tagged).
Figure 3:
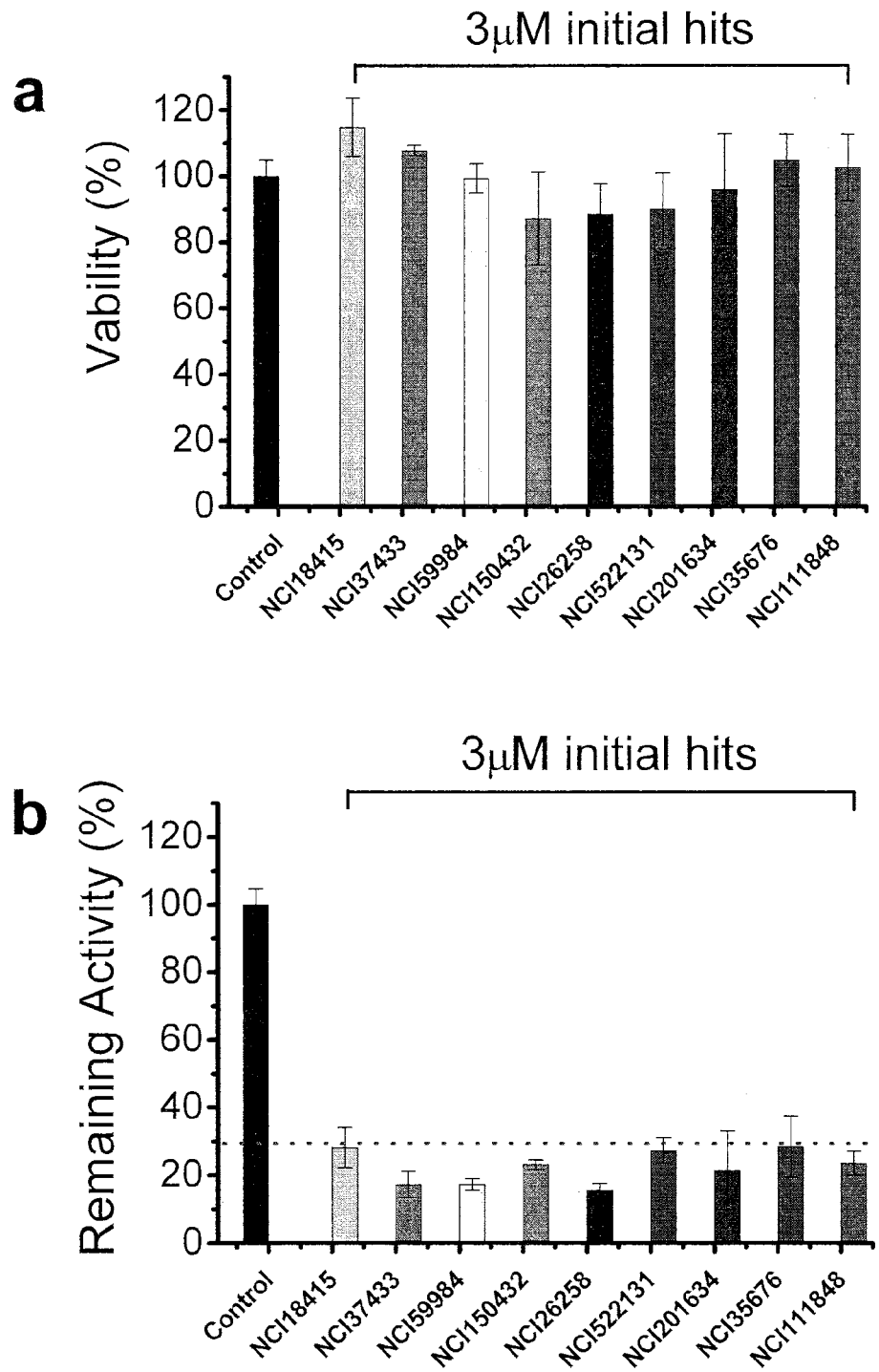
FIG. 3.
Figure 4:
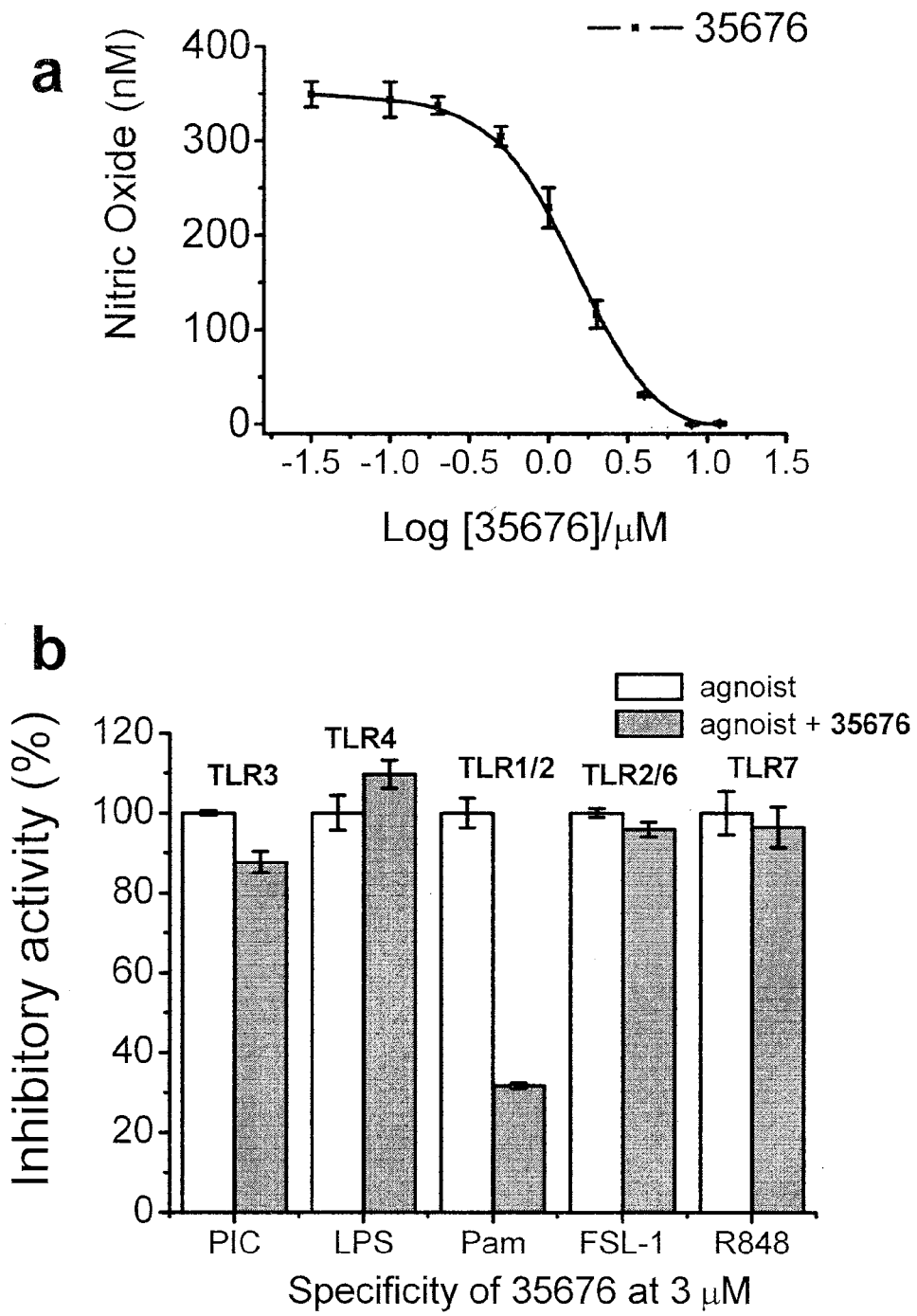
FIG. 4. Dose-dependent inhibitory activity and specificity of NCI35676.

Nine initial hits were identified (FIG. 3) that inhibited TLR1/2 activity by at least 70% at 3.0 µM with no significant cytotoxicity (FIG. 3). The most potent compound was NCI35676, which showed a half-maximal inhibitory concentration ($IC_{50}$) of 2.45±0.25 µM (FIG. 4 and Table 2). The specificity evaluation indicated that out of nine compounds, only NCI35676 specifically inhibited TLR1/2 signaling, and no other homologous TLRs (FIG. 4).

Structure-Activity Relationship Study

A series of NCI35676 analogs were designed to explore the structure-activity relationship (SAR) around the benzotropolone scaffold using a modification of previously developed synthetic methods. See Kerschensteiner et al., *Crocipodin, a benzotropolone pigment from the mushroom Leccinum crocipodium (Boletales)*, Tetrahedron (20110), 67:1536-39, which is herein incorporated by reference in its entirety (FIG. 5). Generally, a one-pot reaction with sequential addition of (a) phosphate-citrate buffer (pH=5), (b) horseradish peroxidase, and (c) 3% $H_2O_2$ produces the bicyclic scaffold. This method provides a concise general synthetic route that can afford the benzotropolone derivative with a yield between about 15% and about 60%. Compound 2 was selected as a representative for the 2D NMR analysis for further analysis and characterization (1H, 13C, HSQC, HMBC and COSY included in FIG. 7).

Further screening of 26 structural analogs yielded additional hits, the most potent being compound 17 (CU-CPT22), which had an IC50 of 0.58±0.09 The improved $IC_{50}$ of the top inhibitor, compound 17, appears to be due to the addition of a six carbon aliphatic chain at the "R6" position, which likely allows for an increase of the hydrophobic contacts to the surface residues of the TLR1/2 complex.

Additionally, the SAR for this series indicated that the amount of total hydroxyl groups were critical. Methylation of one hydroxyl group at the "R1" position had no significant influence to its activity (compound 4), while methylation all the four hydroxyl groups resulted in significant decrease of inhibition (compound 6) (Table 2). Introduction of –F at the "R1" position decreased the activity about 20 fold, which indicates an electron-withdrawing group was not tolerated. The seven-membered ring configuration in benzotropolone scaffold plays an important role for inhibitory activity as determined by Diels-Alder [4+2]-cycloaddition reaction (compound 6 vs. compound 25, compound 9 vs. compound 26). In the following SAR study, the methoxy group was fixed at the "R1" position. With this change, no decrease in activity was observed and no by-products in the synthesis were detected (when R1=OH by-products were detected) (FIG. 5). Meanwhile, the seven-membered ring in the benzotropolone scaffold was kept and substituent groups were introduced at the "R6" position. The addition of a carboxyl group at the "R6" position decreased the activity six-fold (compound 4 vs. compound 10), while methylation of this carboxyl group (compound 11) returned the activity to the NCI35676 level, indicating that "R6" may be critical for the activity.

By introducing ethyl, isopropyl, or various aliphatic chains at this position, it was found that compound 17 (CU-CPT22), with a six carbon chain possessed the highest inhibitory activity for TLR1/2 (Table 2). This increased inhibition was likely caused by the optimal fit of the six membered carbon chain into the substrate tunnel of the TLR1 hydrophobic region (FIG. 8). When the ester was replaced with the amide group in compound 17, the activity slightly decreased (compound 22) (Table 2). Reducing the carboxyl group to an alcohol or introducing large substitutions at the "R6" position, provided no significant change in activity (compound 23, compound 24). In summary, compound 17 was identified as the lead structure, which shows dose-dependent inhibitory effects blocking $Pam_3CSK_4$-induced TLR1/2 activation with an $IC_{50}$ of 0.58±0.09 µM (FIG. 8).

Biophysical Validation

Biophysical tests were carried out for compound 17, along with the negative control compound 6, to demonstrate that compound 17 directly binds to the dimeric interface of TLR1/2. The TLR2 protein was expressed in the baculovirus insect cell expression system using the methods described by Kuroki et al. See Iwaki et al., *The extracellular Toll-like receptor 2 domain directly binds peptidoglycan derived from Staphylococcus aureus*, J. Biol Chem (2002), 277:24315-20, which is herein incorporated by reference in its entirety. The activity of the TLR2 protein was validated by the fluorescence anisotropy assay. It was demonstrated that compound 17 competes with $Pam_3CSK_4$ for binding to TLR1/2 with an inhibition constant ($K_i$) of 0.41+0.07 µM, which is consistent with its potency observed in the whole cell assay. The anisotropy of rhodamine-labeled $Pam_3CSK_4$ showed a robust increase from 0.168 to 0.275 upon addition of TLR1/2 (excitation=549 nm; emission=566 nm (Invivogen)). This increase is consistent with the anisotropy changes seen with ligand-receptor pairs of comparable sizes. Increasing compound 17's concentration to 6 µM decreased the anisotropy to background levels, presumably due to release of the fluorescently labeled $Pam_3CSK_4$ probe. This data was then fit to a one-site-competition model. Good fitting (R2>0.98) inferred that compound 17 and $Pam_3CSK_4$ compete for the same binding site on the TLR1/2 dimeric surface. Compound 6 was used as negative control in the anisotropy assay and demonstrated an $IC_{50}$ of >40 µM (Table 1). These results further support that compound 17 can compete with $Pam_3CSK_4$ binding to TLR1/2.

Specificity

One challenge to developing inhibitors to target TLRs is to engineer specificity and potency. There are at least 13 homologous TLRs present in murine macrophages, all sharing a ligand-binding domain with a double-horseshoe shape. Compound 17 was therefore tested against a panel of homologous TLRs, including TLR1/2, TLR2/6, TLR3, TLR4, and TLR7 using TLR-specific ligands to selectively activate a particular TLR signaling pathway. Compound 17 was found to inhibit TLR1/2 signaling without affecting other TLRs, showing it is highly selective in intact cells (FIG. 8).

Furthermore, compound 17 was found to have no significant cytotoxicity at the active dose. The low toxicity of CU-CPT22 was also confirmed in RAW 264.7 cells using the established MTT methodology.

Computational Modeling

It is worth noting that compound 17 can inhibit TLR1/2, while no significant inhibition to TLR2/6 is observed at 0.5 µM. Based on these experimental observations, computational modeling was conducted to illustrate the potential binding model of CU-CPT22 with TLR1/2. Comparing the crystal structure of TLR1/TLR2/$Pam_3CSK_4$ (FIG. 1a) and TLR2/TLR6/$Pam_2CSK_4$ (FIG. 1b), two lipid chains of $Pam_3CSK_4$ and $Pam_2CSK_4$ interact With the hydrophobic channel in TLR2, and the amide-bound lipid chain of $Pam_3CSK_4$ lies in the hydrophobic channel of TLR1, which does not exist between $Pam_2CSK_4$ and TLR6. The specificity of compound 17 for TLR1/2 is probably caused by the hydrophobic interactions between the hydrophobic chain at "R6" of the compound and the hydrophobic channel of TLR1 (FIG. 8). The predicted binding model is in good agreement with the results of the TLR specificity tests.

Methods

General Methods

NMR spectra were acquired on Bruker 300 or 400 spectrometers, running at 300 MHz (or 400 MHz) for $^1$H and 75 (or 101 MHz) for $^{13}$C, respectively. $^1$H NMR spectra were recorded at 300 MHz in $CDCl_3$, $(CD_3)_2CO$, $(CD_3)_2SO$ or $CD_3CN$ using residual $CHCl_3$ (7.28 ppm), $(CH_3)_2CO$ (2.05 ppm), $(CH_3)_2SO$ (2.50 ppm) and $CH_3CN$ (1.94 ppm) as the internal standard. $^{13}$C NMR spectra were recorded at 75 MHz in $CDCl_3$, $(CD_3)_2CO$ or $(CD_3)_2SO$ using residual $CHCl_3$ (77.16 ppm), $(CH_3)_2CO$ (29.84 and 206.26 ppm), $(CH_3)_2SO$ (39.97 ppm) and $CH_3CN$ (1.32 and 118.26 ppm), as internal reference. Thin layer chromatography was performed on Merck Kieselgel 60 Å F254 or Silicycle 60 Å F254 plates eluting with the solvent indicated, visualized by a 254 nm UV lamp, and stained with an ethanolic solution of 12-molybdophosphoric acid. Compounds were purified using flash chromatography (FC) (Silica gel 60, 200-400 mesh, Sorbent Tech.) or recrystallization. Mass spectrometry was performed at the mass spectrometry facility of the Department of Chemistry at University of Colorado at Boulder on a double focusing high resolution mass spectrometer.

In Vitro TLR1/2 Inhibition Assay

RAW 264.7 (Mouse leukaemic monocyte macrophage cell line) cells were grown in RPMI 1640 medium, supplemented with 10% FBS, penicillin (100 U/mL) and streptomycin (100 mg/mL). RAW cells were then planted in 96-well plates at 80,000 cells per well and grown for 24 h in the media descried previously at 37° C. in a 5% $CO_2$ humidified incubator. After 24 h, non-adherent cells and media were removed and replaced with fresh unsupplemented RPMI 1640 medium. The adherent macrophages were treated with $Pam_3CSK_4$ (CAS No. 112208-00-1; a synthetic triacylated lipopeptide (LP) that mimics the acylated amino terminus of bacterial LPs) (200 ng/mL) (Invivogen, USA), an agonist of TLR1/2, and then added different concentrations of potential inhibitor. Two rows were only treated with $Pam_3CSK_4$ as control. Plates were then incubated for an additional 24 h. Following incubation 100 μL of media was removed and added to flat black 96-well microfluor plates (Thermo Scientific, MA, USA). To each well, 10 μL of 2,3-diaminophthalene (0.05 mg/mL in 0.62 M aqueous HCl solution) was added and incubated for 15 min in the dark. The reaction was quenched by addition of 5 μL of a 3 M aqueous NaOH solution and the plate was read on Beckman Coulter DTX880 reader (Beckman Coulter, Calif., USA) with excitation at 365 nm and emission at 450 nm. The nitrite (a stable metabolite of nitric oxide) concentration was determined from a nitrite standard curve. The inhibition rate (%) of NO release was determined using the following formula: Inhibition (%)=[$Pam_3CSK_4(OD_{450})$ Compounds $(OD_{450})$]/[$Pam_3CSK_4$ $(OD_{450})$–Control $(OD_{450})$]×100. The $IC_{50}$ values for both inhibition and cytotoxicity were determined graphically using software Origin v7.5.

Cytokine-Specific ELISA

RAW 264.7 cells were planted in 6-well plates at 1,000,000 cells per well with 3 mL of medium (RPMI 1640 medium, supplemented with 10% FBS, penicillin (100 U/mL) and streptomycin (100 mg/mL)) and grown for 24 h at 37° C. in a 5% $CO_2$ humidified incubator. After 24 h, non-adherent cells and media were removed and replaced with fresh RPMI 1640 medium (3 mL/well). Two wells of adherent macrophages were treated with $Pam_3CSK_4$ (Invivogen, 300 ng/mL) as the positive control, two wells was treated with 8 μM compound 17, and the other two wells ware treated with 8 μM compound DMSO. Another 6 well plate were treated with $Pam_3CSK_4$ (Invivogen, 300 ng/mL) and different concentration of 17. Plates were then incubated for an additional 24 h. The medium was removed, the cells were washed with PBS (3×1 mL), 6 well plates was put on ice, then 500 μL of lysis buffer was added in each well (Lysis Buffer: 120 μL 0.5M EDTA; 12 mL Mammalian Protein Extraction Reagent, 100 μL cocktail, 0.36 mL NaCl (5 M, aqueous)). After 5 min, the mixture was transferred into corresponding 1.5 mL tube, spun for 20 min at 13.2 K rpm in a cold room. Approximately 400 μL of supernatant were collected into new tubes, frozen at −80° C. until ready for cytokine measurement. The production of the cytokine interleukin-1β (IL-1β) and TNF-α was quantified with enzyme-linked immunosorbent assays (ELISA) using cytokine-specific capture antibodies, biotinylated monoclonal detection antibodies, and recombinant human cytokine standards according to commercially available ELISA kits from R&D Systems. The cytokine level in each sample was determined in duplicate.

RAW 264.7 Cells Nitric Oxide TLR Selectivity Assay

This assay was run in a similar manor as the "In Vitro TLR1/2 Inhibition Assay". High molecule weight Poly (I:C), LPS (lipopolysaccharide), FSL-1 (Synthetic diacylated lipoprotein—TLR2/TLR6 ligand commercially available from Invivogen, USA), and R848 (4-amino-2-(ethoxymethyl)-α) were used to selectively activate TLR3, TLR4, TLR2/6 and TLR7 in place of $Pam_3CSK_4$, respectively.

TLR2 Protein Expression and Purification

The TLR2 protein was expressed in the baculovirus insect cell expression system using the methods described by Kuroki et al. Monolayers of *Spodopera frugiperda* (Sf-9) cells were cotransfected with Bright Baculovirus DNA (BD BaculoGold™) and the pVL1393 plasmid vector containing cDNA for TLR2. Viral titers were amplified to ~5-10×10$^7$/mL virus particles. The recombinant viruses were used to infect suspension high 5 insect cells in serum-free medium (Insect-XPRESS™ Protein-free Insect Cell Medium with L-glutamine, Lonza) at 27° C., 130 rpm. After incubation of high 5 insect cells with recombinant viruses for 3 days, the cells changed to green (Supplementary Figure S7a, S7b), the medium was collected after low-speed centrifugation and dialyzed (Slide-A-Lyzer G2 Dialysis Cassettes, 10K MWCO, Pierce) against 0.1 M Tris buffer (pH 8.0) containing 0.3 M NaCl. The dialyzed medium was filtered and purified by a column of nickelnitrilotriacetic acid beads (Qiagen, Santa Clarita, Calif.) according to the manufacturer's instruction. The purified protein was finally dialyzed against 5 mM Tris buffer (pH 7.4) containing 0.15 M NaCl and condensed by centrifugal concentrator (Millipore 10,000 MWCO). Electrophoretic analysis revealed that TLR2 exhibited a single band with a molecular mass of 75 kDa (Supplementary Figure S7c). Approximately 100 ng of TLR2 protein was obtained from 500 mL of medium.

Fluorescence Anistropy Assay

In 500 μL Tris buffer (pH=7.2) add 10 μL, (1 ng/mL) rhodamine-labeled $Pam_3CSK_4$, test the fluorescence anisotropy at excitation of 549 nm and emission of 566 nm (Horiba Fluorolog 3). And 5 μL (20 μM) TLR1 (R &D) and 5 μL, (20 μM) TLR2 was added into the above buffer, then retest the anisotropy. Following, compound 17 or compound 6 was added in the buffer from the concentration of 0 to 6 μM, and the fluorescence anisotropy was tested in the corresponding concentration.

Fluorescence polarization experiments were performed at 25° C. using a Horiba Fluorolog-3 fluorometer. For direct binding measurements, serial dilutions of TLR1 (R&D, MN) and TLR2 were made in Tris buffer (pH=7.2), and an aliquot (10 μL) of 1 ng/mL rhodamine labeled $Pam_3CSK_4$, was added to a total volume of 500 μL. The competition binding solution was incubated for 30 minutes at 25° C. Serial dilutions of compound 17 or compound 6 were incubated with 20 μM TLR1, 20 μM TLR2 and rhodamine-labeled $Pam_3CSK_4$ for 30 min at room temperature.

Regression analysis was carried out using Origin 7.5 (OriginLab) ligand binding macro module. Experimental data were fitted into equation (1) to determine the $IC_{50}$ values, which in turn can be related to the known affinity of the $Pam_3CSK_4$ ($K_d$=1.2 nM) to acquire the inhibitory constant $K_i$ using equation (2). Equation (1): $y=min+(max-min)/(1+10^{x-logIC50})$ (total binding, x=log concentration of and rhodamine-labeled $Pam_3CSK_4$, min=nonspecific binding, max=maximum binding in absence of ligand). Equation (2): $K_i=IC_{50}/(1+[L]/K_d)$ ([L]=concentration of rhodamine-labeled $Pam_3CSK_4$).

In Vitro Cytotoxicity Assay.

MTT Cytotoxicity Assay. In a 96-well plate 10,000 cells in 200 µL media (RPMI 1640 medium, supplemented with 10% FBS, penicillin (100 U/mL) and streptomycin (100 mg/mL)) per well. Eight wells were left empty for blank controls. The plates were incubated (37° C., 5% $CO_2$) overnight to allow the cells to attach to the wells. Add 20 ul (5 mg/mL) MTT solution to each well. Place on a shaking table, 150 rpm for 5 minutes, to thoroughly mix the MTT into the media. Incubate (37° C., 5% $CO_2$) for 4 hours to allow the MTT to be metabolized. Dump off the media. Dry plate on paper towels to remove residue. Resuspend formazan (MTT metabolic product) in 200 ul DMSO. Place on a shaking table, 150 rpm for 5 minutes, to thoroughly mix the formazan into the solvent. When a clear difference could be seen by naked eye, results were read by spectrophotometer at 560 nm. Optical density should be directly correlated with cell quantity. Cytotoxicity (%) was determined using the following formula: Cytotoxicity (%) (1−[Compounds $(OD_{560})$−Background$(OD_{560})$]/[Control $(OD_{560})$−Background $(OD_{560})$])×100.

In Silico Docking.

Compound 17 was docked into the TLR1/TLR2 binding domain (PDB: 2Z7X$^J$) using Glide 5.6. The molecule was created, as appropriate, with multiple protonation and tautomeric states. The TLR1/2 conformations were prepared using standard Glide protocols. This includes addition of hydrogens, restrained energy-minimizations of the protein structure with the Optimized Potentials for Liquid Simulations-All Atom (OPLS-AA) force field, and finally setting up the Glide grids using the Protein and Ligand Preparation Module.

Synthesis Method

Method I

A: Catechol (110 mg, 1.00 mmol) and pyrogallol (126 mg, 1.00 mmol) were dissolved in a mixture of acetone-pH 5.0 phosphate-citrate (1:1=0.2 M $Na_2HPO_4$: 0.1 M citrate) buffer (1:5 v/v, 5 mL), which contained 0.1 mg horseradish peroxidase (cas 9003-99-0, 5KU, Fisher). Four aliquots of 3% $H_2O_2$ (2 mL each) were added every 10 min over 40 min while stirring. After 2-3 h, the resulting orange precipitate was filtered off, washed with water (3×6 mL) and dried under high vacuum condition to give a mixture of 2 and NCI35676 (purpurogallin). The mixture was purified by flash chromatography on silica gel, using ethyl acetate/hexane (1:4) as eluent, to give 2 as an orange solid (23 mg, 11%).

B: Using 3-methoxycatechol (140 mg, 1.00 mmol) instead of catechol and gallic acid (170 mg, 1.00 mmol) instead of the pyrogallol, gave the single orange solid product 10 (160 mg, 57%).

Method II

To a suspension of purpurogallin (44 mg, 0.200 mmol) and anhydrous $K_2CO_3$ (332 mg, 2.40 mmol) in anhydrous DMF (8 mL), maintained at 0° C. under nitrogen, was added dropwise iodomethane (99 µL, 1.6 mmol), and the mixture was stirred overnight at room temperature. After this time, the reaction was quenched with water (10 mL) and the mixture stirred for 20 min. After addition of EtOAc (20 mL), the organic phase was washed with water (3×20 mL), and the combined aqueous phases were extracted with EtOAc (20 mL). The organic extracts were dried over $Na_2SO_4$ and concentrated under reduced pressure. Purified by flash chromatography on silica gel, using ethyl acetate/hexane (1:5) as eluent, gave 6 as white solid (49 mg, 89%).

A solution of 6 (28 mg, 0.101 mmol) and maleic anhydride (36.0 mg, 0.200 mmol) in toluene (2 mL) was heated to reflux in a sealed schlenk tube for 24 h. The mixture was then evaporated to dryness under reduced pressure, and the resulting crude solid was purified by flash chromatography on silica gel, using ethyl acetate/hexane (1:6) as eluent, to give 25 as white solid (28 mg, 75%).

Method III

Acetic anhydride (56.7 µL, 0.600 mmol) was added slowly over a period of 30 min to a stirred solution of purpurogallin (44 mg, 0.200 mmol) in 2 mL of pyridine at 110° C. After an additional 12 h, 10 mL 1M HCl was added, and then extracted with dichloromethane (3×15 mL). The combined organic phases were dried over $Na_2SO_4$, filtered, and concentrated to give a yellow solid. This was purified by flash chromatography on silica gel, using ethyl acetate/hexane (1:5) as eluent, to give 8 as a yellow powder (43 mg, 54%).

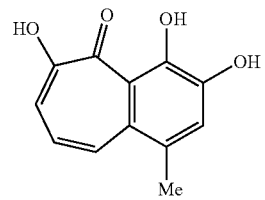 [SMILES: Cc1cc(O)c(O)c2c(=O)c(O)cccc12]

3,4,6-trihydroxy-1-methyl-5H-benzo[7]annulen-5-one (1)

Following the general method IA, using 4-methylbenzene-1,2-diol (124 mg, 1.00 mmol) instead of catechol, gave an orange solid. The solid mixture was purified by flash chromatography on silica gel, using ethyl acetate/hexane (1:4) as eluent, to give 1 as an orange solid (23 mg, 10%): $^1$H NMR (300 MHz, DMSO) δ 14.91 (s, 1H), 9.64 (s, 2H), 7.60 (d, J=11.8 Hz, 1H), 7.40 (s, 1H), 7.19 (d, J=9.3 Hz, 1H), 6.83 (dd, J=11.8, 9.5 Hz, 1H), 3.39 (s, 3H); $^{13}$C NMR (75 MHz, DMSO) δ 185.01, 155.37, 149.33, 146.02, 130.38, 129.55, 129.42, 125.25, 123.14, 121.71, 118.64, 22.17; LRMS (ESI): calcd for: $C_{12}H_{10}O_4$ [M+Na]$^+$=241.2, obsd [M+Na]$^+$=241.0.

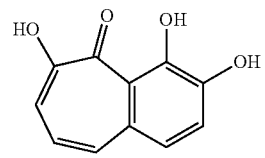 [SMILES: O=c1c(O)cccc2ccc(O)c(O)c12]

3,4,6-trihydroxy-5H-benzo[7]annulen-5-one (2)

Following the general method IA, gave 2 as an orange solid (23 mg, 11%): $^1$H NMR (300 MHz, DMSO) δ 14.97 (s, 1H), 9.86 (s, 1H), 9.53 (s, 1H), 7.45 (td, J=14.4, 10.1 Hz, 3H), 7.19 (dd, J=9.5, 0.8 Hz, 1H), 6.77 (dd, J=11.3, 9.5 Hz, 1H); $^{13}$C NMR (75 MHz, DMSO) δ 184.82, 155.15, 150.89, 146.56, 135.95, 131.88, 125.50, 123.27, 122.72, 120.66, 119.04; LRMS (ESI): calcd for: $C_{11}H_8O_4$ [M+Na]$^+$=227.1, obsd [M+Na]$^+$=227.0.

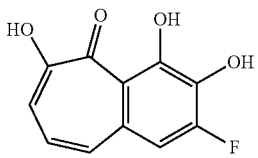 [SMILES: O=c1c(O)cccc2cc(F)c(O)c(O)c12]

2-fluoro-3,4,6-trihydroxy-5H-benzo[7]annulen-5-one (3)

Following the general method IA, using 3-fluorocatechol (128 mg, 1.00 mmol) instead of catechol, gave an orange solid. The mixture was purified by flash chromatography on silica gel, using ethyl acetate/hexane (1:4) as eluent, to give 3 as an orange solid (20 mg, 9%): $^1$H NMR (300 MHz, DMSO) δ 15.45 (s, 1H), 9.81 (s, 2H), 7.53-7.37 (m, 2H), 7.19 (dd, J=9.6, 0.7 Hz, 1H), 6.86 (dd, J=11.4, 9.6 Hz, 1H); $^{13}$C NMR (75 MHz, DMSO) δ 184.20, 155.77, 154.17, 152.58, 134.70, 132.41, 124.98, 118.61, 118.17, 110.76, 110.50; HRMS (ESI): calcd for: $C_{11}H_7FO_4$ [M−H]$^−$=221.0255, obsd [M−H]$^−$=221.0255.

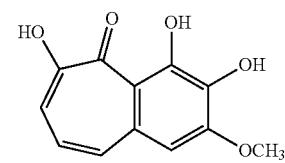 [SMILES: COc1cc2cccc(O)c(=O)c2c(O)c1O]

3,4,6-trihydroxy-2-methoxy-5H-benzo[7]annulen-5-one (4)

Following the general method IA, using 3-methoxycatechol (140.1 mg, 1 mmol) instead of catechol, get an orange solid mixture. The mixture was purified by flash chromatography on silica gel, using ethyl acetate/hexane (1:4) as eluent, to give 4 as an orange solid (26 mg, 11%): $^1$H NMR (300 MHz, DMSO) δ 15.14 (s, 1H), 9.50 (s, 1H), 9.38 (s, 1H), 7.52 (d, J=11.2 Hz, 1H), 7.21-7.11 (m, 2H), 6.83 (dd, J=11.3, 9.5 Hz, 1H), 3.97 (s, 3H); $^{13}$C NMR (75 MHz, DMSO) δ 183.00, 155.57, 152.74, 151.27, 135.85, 135.13, 133.26, 124.36, 117.53, 116.51, 106.97, 56.37; LRMS (ESI): calcd for: $C_{12}H_{10}O_5$ [M−H]$^−$=233.1, obsd [M−H]$^−$=233.0.

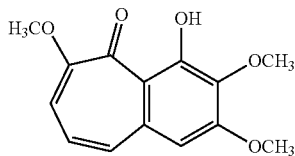 [SMILES: COc1cc2cccc(OC)c(=O)c2c(O)c1OC]

4-hydroxy-2,3,6-trimethoxy-5H-benzo[7]annulen-5-one (5)

Following the general method II, to a suspension of purpurogallin (44 mg, 0.200 mmol) and anhydrous $K_2CO_3$ (249 mg, 1.80 mmol) in anhydrous DMF (8 mL), maintained at 0° C. under nitrogen, was added dropwise iodomethane (62 μL, 1.00 mmol), and the mixture was stirred overnight at room temperature. Then, the reaction was quenched with water (10 mL) and the mixture was stirred for an additional 20 min. After addition of EtOAc (20 mL), the organic phase was washed with water (3×20 mL), and the combined aqueous phases were extracted with EtOAc (20 mL). The organic extracts were dried over $Na_2SO_4$ and concentrated under reduced pressure. The resulting solid was purified by flash chromatography on silica gel, using ethyl acetate/hexane (1:6) as eluent, give 5 as white solid (36 mg, 70%): $^1$H NMR (300 MHz, DMSO) δ 15.27 (s, 1H), 7.40 (d, J=10.9 Hz, 1H), 7.08 (s, 1H), 6.85 (dt, J=11.1, 9.3 Hz, 2H), 3.96 (s, 3H), 3.83 (s, 3H), 3.78 (s, 3H); $^{13}$C NMR (75 MHz, DMSO) δ 185.62, 158.58, 157.95, 157.02, 136.66, 136.30, 134.41, 124.56, 117.50, 114.00, 106.64, 60.11, 56.69, 56.46; HRMS (ESI): calcd for: $C_{14}H_{14}O_5$ [M+H]$^+$=263.0914, obsd [M+H]$^+$=263.0914.

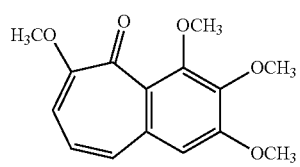 [SMILES: COc1cc2cccc(OC)c(=O)c2c(OC)c1OC]

2,3,4,6-tetramethoxy-5H-benzo[7]annulen-5-one (6)

Following the general method II, gave 6 as white solid (49 mg, 89%): $^1$H NMR (300 MHz, DMSO) δ 7.07 (s, 1H), 7.02 (d, J=11.7 Hz, 1H), 6.56 (dd, J=11.6, 8.6 Hz, 1H), 6.29 (d, J=8.7 Hz, 1H), 3.91 (s, 1H), 3.84 (s, 1H), 3.79 (s, 1H), 3.72, (s, 1H); $^{13}$C NMR (75 MHz, DMSO) δ 184.58, 158.40, 155.27, 152.06, 143.30, 132.57, 128.73, 125.16, 123.95, 107.74, 105.23, 62.63, 61.02, 56.44, 56.18; HRMS (ESI): calcd for: $C_{15}H_{16}O_5$ [M+H]$^+$=277.1066, obsd [M+H]$^+$=277.1070.

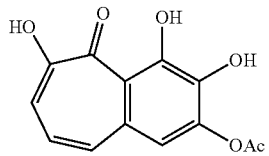 [SMILES: CC(=O)Oc1cc2cccc(O)c(=O)c2c(O)c1O]

3,4,6-trihydroxy-5-oxo-5H-benzo[7]annulen-2-yl acetate (7)

Following the general method III, using fewer equivalence of acetic anhydride (18.9 μL, 0.200 mmol) in the reaction, gave an orange solid mixture. The resulting solid was purified by flash chromatography on silica gel, using ethyl acetate/hexane (1:5) as eluent, to give 7 as an orange powder (12 mg, 23%): $^1$H NMR (300 MHz, DMSO) δ 15.53 (s, 1H), 11.23 (s, 1H), 9.71 (s, 1H), 7.38 (t, J=13.5 Hz, 1H), 7.07 (d, J=8.9 Hz, 1H), 6.87 (dd, J=10.9, 9.0 Hz, 2H), 2.32 (s, 3H); $^{13}$C NMR (75 MHz, DMSO) δ 183.57, 168.48, 158.20, 156.36, 155.72, 138.93, 134.08, 127.02, 126.98, 116.78, 115.03, 110.07, 20.79; HRMS (ESI): calcd for: $C_{13}H_{10}O_6$ [M−H]$^−$=261.0397, obsd [M−H]$^−$=261.0404.

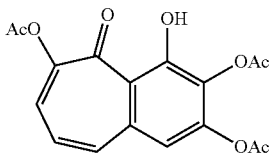 [SMILES: CC(=O)Oc1cc2cccc(OC(C)=O)c(=O)c2c(O)c1OC(C)=O]

4-hydroxy-5-oxo-5H-benzo[7]annulene-2,3,6-triyl triacetate (8)

Following the general method III, gave 8 as a yellow powder (43 mg, 54%): $^1$H NMR (300 MHz, DMSO) δ 14.96, δ 7.75-7.68 (m, 1H), 7.57-7.50 (m, 2H), 6.95 (dd, J=11.5, 9.1 Hz, 1H), 2.38 (s, 1H), 2.37 (s, 1H), 2.32 (s, 1H); $^{13}$C NMR (75 MHz, CDCl$_3$) δ 184.96, 168.84, 167.39, 167.36, 159.10, 150.57, 147.22, 140.21, 136.21, 132.11, 129.37, 123.20, 120.62, 117.88, 20.76, 20.55, 20.29; FIRMS (ESI): calcd for: $C_{17}H_{14}O_8$ [M–H]$^-$=345.1, obsd [M–H]$^-$=345.1.

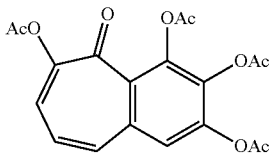 [SMILES: CC(=O)Oc1cc2cccc(OC(C)=O)c(=O)c2c(OC(C)=O)c1OC(C)=O]

5-oxo-5H-benzo[7]annulene-2,3,4,6-tetrayl tetraacetate (9)

Following the general method III, using more equivalence of acetic anhydride (18.9 μL, 0.200 mmol) in the reaction, get a light yellow solid. This was purified by flash chromatography on silica gel, using ethyl acetate/hexane (1:5) as eluent, to give 9 as a light yellow powder (43.7 mg, 56%): $^1$H NMR (300 MHz, DMSO) δ 7.84 (s, 1H), 7.47 (dd, J=12.3, 0.7 Hz, 1H), 7.11 (dd, J=8.7, 0.7 Hz, 1H), 6.81 (dd, J=11.6, 8.7 Hz, 1H), 2.39-2.32 (m, 6H), 2.27 (s, 3H), 2.25 (s, 3H); $^{13}$C NMR (75 MHz, DMSO) δ 180.87, 168.43, 168.17, 168.13, 167.64, 149.55, 145.48, 143.63, 137.23, 135.06, 134.26, 128.21, 124.70, 124.18, 123.79, 20.86, 20.59, 20.31; HRMS (EST): calcd for: $C_{19}H_{16}O_9$ [M+H]$^+$=389.0857, obsd [M+H]$^+$=389.0867.

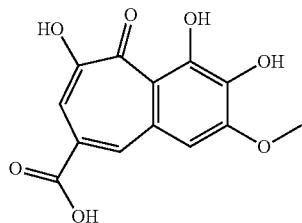 [SMILES: COc1cc2cc(C(=O)O)cc(O)c(=O)c2c(O)c1O]

3,4,6-trihydroxy-2-methoxy-5-oxo-5H-benzo[7]annulene-8-carboxylic acid (10)

Following method IB, gave the orange solid product 10 (160 mg, 57%): $^1$H NMR (300 MHz, DMSO) δ 14.99 (s, 1H), 13.41 (s, 1H), 9.83 (s, 1H), 9.65 (s, 1H), 8.65-8.18 (m, 1H), 7.63 (d, J=1.5 Hz, 1H), 7.45 (s, 1H), 4.00 (s, 3H); $^{13}$C NMR (75 MHz, DMSO) δ 183.52, 168.14, 154.00, 152.49, 151.84, 138.49, 137.96, 130.51, 124.99, 116.74, 115.12, 110.19, 56.66; LRMS (ESI): calcd for: $C_{13}H_{10}O_7$ [M–H]$^-$=277.1, obsd [M–H]$^-$=277.0.

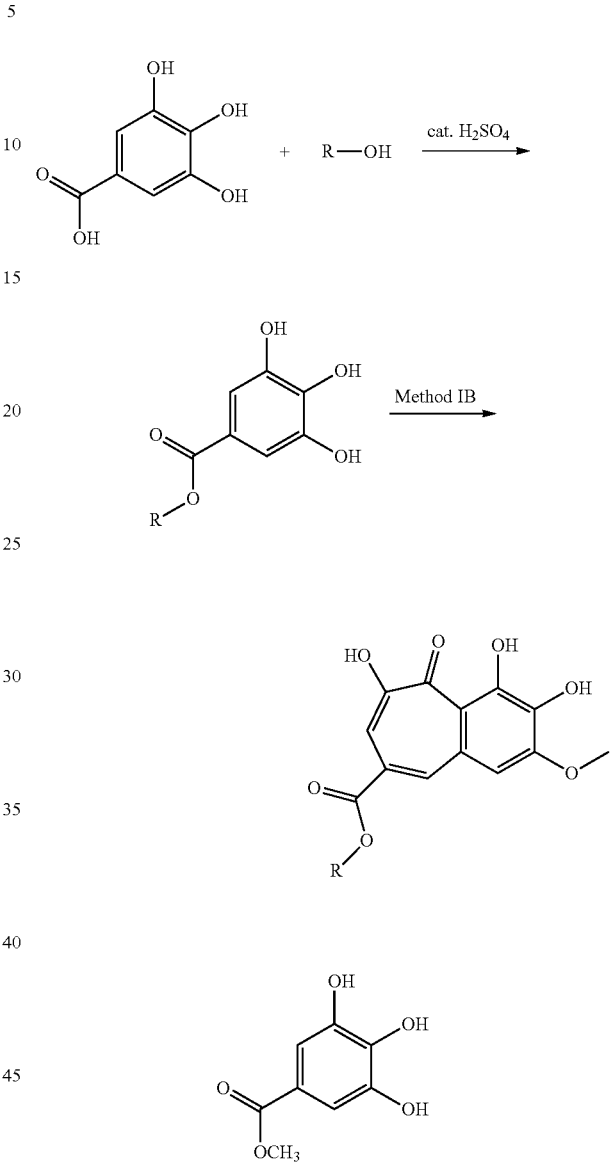

Methyl 3,4,5-trihydroxybenzoate

Gallic acid (850.6 mg, 5 mmol) and dissolved in MeOH (10 mL). Then, conc. H$_2$SO$_4$ (272.7 μL, 11 mmol) was added to the solution and was stirred at reflux for 12 h (monitored by TLC). The solvent was concentrated under reduced pressure. After extraction with EtOAc (20 mL), the solution was washed with distilled water (3×10 mL) and saturated NaHCO$_3$ (20 mL), and dried over Na$_2$SO$_4$. The solution was evaporated and purified by flash chromatography on silica gel, using ethyl acetate/hexane (1:2) as eluent, to give methyl 3,4,5-trihydroxybenzoate as a white powder (782.6 mg, 85%): $^1$H NMR (300 MHz, MeOD) δ 7.06 (s, 2H), 4.98 (s, 3H), 3.82 (s, 3H); $^{13}$C NMR (75 MHz, DMSO) δ 166.76, 146.09, 146.02, 138.84, 119.73, 108.94, 52.04.

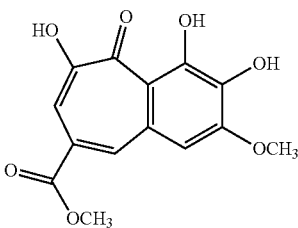 [SMILES: COC(=O)c1cc(O)c(=O)c2c(O)c(O)c(OC)cc2c1]

Methyl 3,4,6-trihydroxy-2-methoxy-5-oxo-5H-benzo[7]annulene-8-carboxylate (11)

Following the general method IB, using methyl 3,4,5-trihydroxybenzoate (185 mg, 1.00 mmol) instead of gallic acid, gave the orange precipitate. The resulting orange precipitate was filtered off, washed with water (3×6 mL) and dried under high vacuum to give the orange solid product 11 (172 mg, 59%): $^1$H NMR (300 MHz, DMSO) δ 14.94 (s, 1H), 9.90 (s, 1H), 9.73 (s, 1H), 8.39 (d, J=1.2 Hz, 1H), 7.58 (d, J=1.6 Hz, 1H), 7.47 (s, 1H), 4.01 (s, 3H), 3.90 (s, 3H); $^{13}$C NMR (75 MHz, DMSO) δ 183.60, 167.11, 154.19, 152.49, 151.91, 138.52, 138.24, 130.23, 123.91, 116.69, 114.49, 110.49, 56.71, 53.42; LRMS (ESI): calcd for: $C_{14}H_{12}O_7$ [M+H]$^+$=293.2, obsd [M+H]$^+$=293.1.

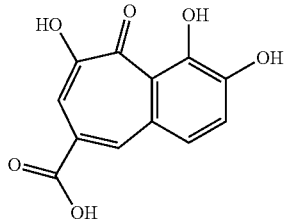 [SMILES: O=C(O)c1cc(O)c(=O)c2c(O)c(O)ccc2c1]

3,4,6-trihydroxy-5-oxo-5H-benzo[7]annulene-8-carboxylic acid (12)

Following the general method IB, using 1,2-benzenediol (101 mg, 1.00 mmol) instead of 3-methoxycatechol, gave 12 as an orange precipitate (121 mg, 49%): $^1$H NMR (300 MHz, DMSO) δ 14.82 (s, 1H), 10.41 (s, 1H), 9.68 (s, 1H), 8.32 (d, J=0.9 Hz, 1H), 7.65 (dd, J=10.3, 5.3 Hz, 2H), 7.48 (d, J=8.6 Hz, 1H); $^{13}$C NMR (75 MHz, DMSO) δ 185.38, 168.07, 153.55, 151.65, 149.04, 139.18, 129.19, 128.64, 123.98, 122.43, 120.79, 116.42; LRMS (ESI): calcd for: $C_{12}H_8O_6$ [M−H]$^−$=247.1, obsd [M−H]$^−$=247.0.

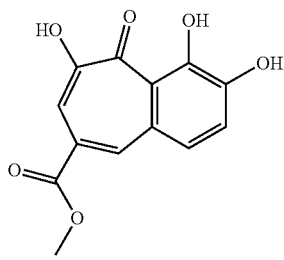 [SMILES: COC(=O)c1cc(O)c(=O)c2c(O)c(O)ccc2c1]

Methyl 3,4,6-trihydroxy-5-oxo-5H-benzo[7]annulene-8-carboxylate (13)

Following 12 synthetic method, using 3,4,5-trihydroxybenzoate (185 mg, 1.00 mmol) instead of gallic acid, gave 13 as an orange precipitate (141 mg, 54%): $^1$H NMR (300 MHz, CDCl$_3$) δ 14.67 (s, 1H), 8.45 (d, J=1.6 Hz, 1H), 8.19 (s, 1H), 8.01 (d, J=1.6 Hz, 1H), 7.55 (s, 2H), 6.54 (s, 1H), 3.99 (s, 311); $^{13}$C NMR (75 MHz, DMSO) δ 185.43, 167.00, 153.68, 151.74, 149.36, 139.24, 128.91, 128.87, 122.81, 122.40, 120.69, 115.68, 53.39; LRMS (ESI): calcd for: $C_{13}H_{10}O_6$ [M−H]$^−$=261.0, obsd [M−H]$^−$=261.0.

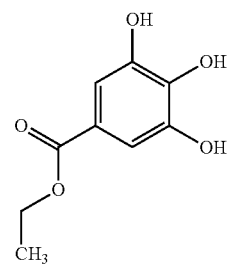

Ethyl 3,4,5-trihydroxybenzoate

Following methyl 3,4,5-trihydroxybenzoate synthetic method, using EtOH (10 mL) instead of MeOH, gave ethyl 3,4,5-trihydroxybenzoate as a white solid (903 mg, 91%): $^1$H NMR (300 MHz, DMSO) δ 9.26 (s, 2H), 8.93 (s, 1H), 6.94 (s, 2H), 4.20 (q, J=7.1 Hz, 2H), 1.27 (t, J=7.1 Hz, 3H); $^{13}$C NMR (75 MHz, DMSO) δ 166.26, 145.99, 138.77, 120.01, 108.89, 60.44, 14.71.

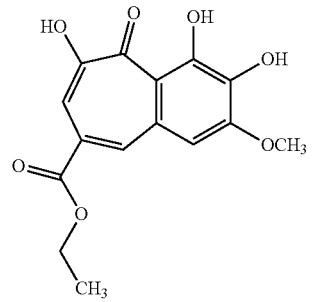 [SMILES: CCOC(=O)c1cc(O)c(=O)c2c(O)c(O)c(OC)cc2c1]

Ethyl 3,4,6-trihydroxy-2-methoxy-5-oxo-5H-benzo[7]annulene-8-carboxylate (14)

Following general method IB, using ethyl 3,4,5-trihydroxybenzoate (198 mg, 1.00 mmol) instead of gallic acid, gave 14 as an orange precipitate (158.6 mg, 51.8%): $^1$H NMR (300 MHz, DMSO) δ 14.95 (s, 1H), 9.89 (s, 1H), 9.72 (s, 1H), 8.37 (d, J=1.6 Hz, 1H), 7.59 (d, J=1.6 Hz, 1H), 7.46 (s, 1H), 4.35 (tt, J=7.1, 3.5 Hz, 2H), 4.01 (s, 3H), 1.37 (t, J=7.1 Hz, 3H); $^{13}$C NMR (75 MHz, DMSO) 183.56, 166.57, 154.15, 152.48, 151.89, 138.44, 138.20, 130.24, 124.16, 116.68, 114.50, 110.44, 62.21, 56.71, 14.62; HRMS (ESI): calcd for: $C_{15}H_{14}O_7$ [M−H]$^−$=305.0668, obsd [M−H]$^−$=305.0666.

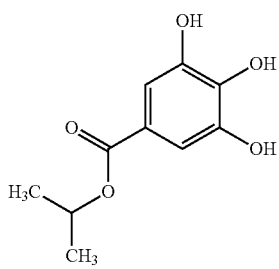

Isopropyl 3,4,5-trihydroxybenzoate

Following the method used for methyl 3,4,5-trihydroxybenzoate, using isopropyl alcohol (10 mL) instead of MeOH, gave isopropyl 3,4,5-trihydroxybenzoate as a white solid (941 mg, 89%): $^1$H NMR (300 MHz, DMSO) δ 9.18 (m, 3H), 6.93 (s, 2H), 5.42-4.82 (m, 1H), 1.26 (m, 6H); $^{13}$C NMR (75 MHz, DMSO) δ 165.75, 145.95, 138.68, 120.39, 108.88, 67.57, 22.20.

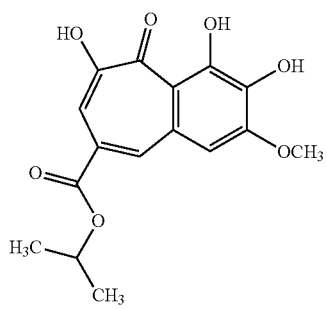 [SMILES: COc1cc2cc(C(=O)OC(C)C)cc(O)c(=O)c2c(O)c1O]

Isopropyl 3,4,6-trihydroxy-2-methoxy-5-oxo-5H-benzo[7]annulene-8-carboxylate (15)

Following general method IB, using isopropyl 3,4,5-trihydroxybenzoate (198 mg, 1.00 mmol) instead of gallic acid, gave 15 as an orange precipitate (157 mg, 49%): $^1$H NMR (300 MHz, DMSO) δ 14.96 (s, 1H), 9.88 (s, 1H), 9.72 (s, 1H), 8.53-8.28 (m, 1H), 7.58 (d, J=1.5 Hz, 1H), 7.45 (s, 1H), 5.30-5.02 (m, 1H), 4.02 (s, 3H), 1.37 (d, 6H); $^{13}$C NMR (75 MHz, DMSO) δ 183.55, 166.06, 154.13, 152.49, 151.88, 138.38, 138.17, 130.27, 124.51, 116.70, 114.54, 110.42, 69.83, 56.73, 22.08; HRMS (ESI): calcd for: $C_{16}H_{16}O_7$ [M–H]$^-$=319.0812, obsd [M–H]$^-$=319.0813.

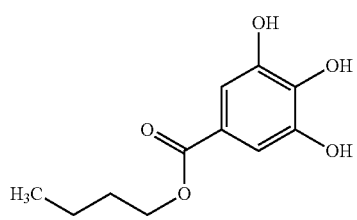 [SMILES: CCCCOC(=O)c1cc(O)c(O)c(O)c1]

Butyl 3,4,5-trihydroxybenzoate

Following the method used for methyl 3,4,5-trihydroxybenzoate, using 1-butanol (10 mL) instead of MeOH, gave butyl 3,4,5-trihydroxybenzoate as a white solid (644 mg, 57%). $^1$H NMR (300 MHz, DMSO) 8.9.25-8.95 (m, 3H), 6.95 (s, 2H), 4.16 (t, J=6.5 Hz, 2H), 1.69-1.56 (m, 2H), 1.48-1.30 (m, 2H), 0.92 (t, J=7.4 Hz, 3H); $^{13}$C NMR (75 MHz, DMSO) δ 166.30, 145.99, 138.78, 120.01, 108.89, 64.12, 30.80, 19.25, 14.06.

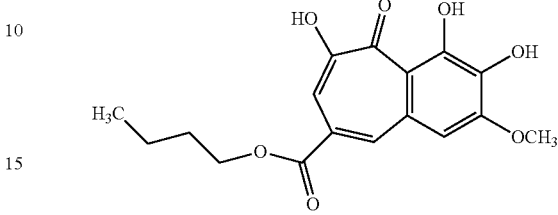

Butyl 3,4,6-trihydroxy-2-methoxy-5-oxo-5H-benzo[7]annulene-8-carboxylate (16)

Following general method IB, using butyl 3,4,5-trihydroxybenzoate (226 mg, 1.00 mmol) instead of gallic acid, gave 16 as an orange precipitate (171 mg, 51%): $^1$H NMR (300 MHz, DMSO) δ 14.95 (s, 1H), 9.89 (s, 1H), 9.73 (s, 1H), 8.36 (d, J=1.1 Hz, 1H), 7.58 (d, J=1.5 Hz, 1H), 7.44 (s, 1H), 4.31 (t, J=6.6 Hz, 2H), 4.01 (s, 3H), 1.82-1.64 (m, 2H), 1.53-1.32 (m, 2H), 0.95 (t, J=7.4 Hz, 3H); $^{13}$C NMR (75 MHz, DMSO) δ 183.57, 166.61, 154.17, 152.49, 151.90, 138.47, 138.22, 130.24, 124.15, 116.70, 114.45, 110.47, 65.89, 56.72, 30.68, 19.17, 14.10; HRMS (ESI): calcd for: $C_{17}H_{18}O_7$ [M–H]$^-$=333.0978, obsd [M–H]$^-$–333.0979.

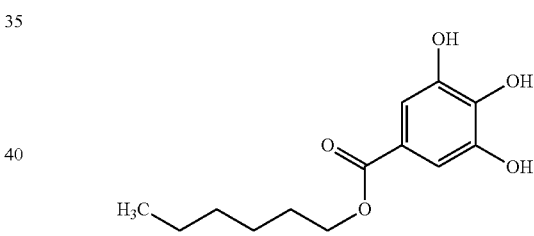

Hexyl 3,4,5-trihydroxybenzoate

Following methyl 3,4,5-trihydroxybenzoate synthetic method, using 1-hexanol (10 mL) instead of MeOH, gave hexyl 3,4,5-trihydroxybenzoate as a white solid (549 mg, 43%): $^1$H NMR (300 MHz, CDCl$_3$) δ 7.35 (s, 2H), 5.99 (s, 3H), 4.29 (t, J=6.6 Hz, 2H), 1.85-1.68 (m, 2H), 1.52-1.24 (m, 6H), 0.92 (dd, J=8.6, 4.3 Hz, 3H); $^{13}$C NMR (75 MHz, Acetone) δ 165.83, 145.08, 137.67, 121.21, 108.81, 64.10, 31.32, 28.60, 25.57, 22.33, 13.38.

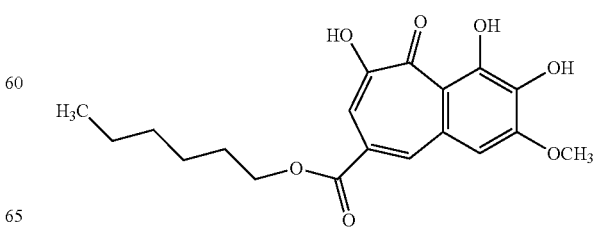

Hexyl 3,4,6-trihydroxy-2-methoxy-5-oxo-5H-benzo[7]annulene-8-carboxylate (17, CU-CPT22)

Following general method IB, using hexyl 3,4,5-trihydroxybenzoate (254 mg, 1.00 mmol) instead of gallic acid to give CU-CPT22 as an orange precipitate (195 mg, 54%): $^1$H NMR (300 MHz, DMSO) δ 14.93 (s, 1H), 9.73 (s, 2H), 8.32 (d, J=1.2 Hz, 1H), 7.56 (d, J=1.5 Hz, 1H), 7.40 (s, 1H), 4.28 (dd, J=8.6, 4.8 Hz, 2H), 4.01 (s, 3H), 1.72 (dd, J=14.5, 6.8 Hz, 2H), 1.52-1.18 (m, 6H), 0.97-0.77 (m, 3H); $^{13}$C NMR (75 MHz, DMSO) δ 183.51, 166.55, 154.13, 152.45, 151.89, 138.45, 138.23, 130.19, 124.11, 116.66, 114.41, 110.40, 66.16, 56.67, 31.34, 28.53, 25.52, 22.45, 14.33; HRMS (ESI): calcd for: $C_{19}H_{22}O_7$ [M−H]$^−$=361.1286, obsd [M−H]$^−$=361.1292.

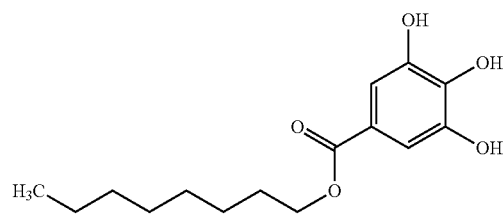 [SMILES: CCCCCCCCOC(=O)c1cc(O)c(O)c(O)c1]

Octyl 3,4,5-trihydroxybenzoate

Following methyl 3,4,5-trihydroxybenzoate synthetic method, using 1-octanol (10 mL) instead of MeOH, gave octyl 3,4,5-trihydroxybenzoate as a white solid (643.7 mg, 46%): $^1$H NMR (300 MHz, DMSO) δ 9.15 (s, 3H), 6.94 (s, 2H), 4.15 (t, J=6.5 Hz, 2H), 1.64 (dd, J=14.2, 6.7 Hz, 2H), 1.45-1.21 (m, 10H), 0.86 (t, 3H); $^{13}$C NMR (75 MHz, DMSO) δ 166.29, 145.99, 138.79, 119.99, 108.88, 64.40, 31.68, 29.11, 29.10, 28.74, 26.00, 22.53, 14.41.

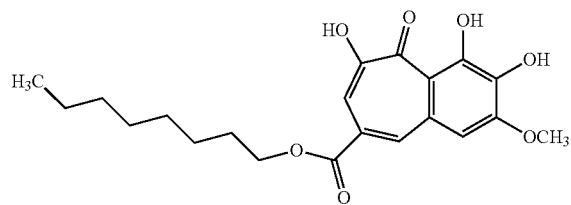 [SMILES: CCCCCCCCOC(=O)c1cc(O)c(=O)c2c(O)c(O)c(OC)cc2c1]

Octyl 3,4,6-trihydroxy-2-methoxy-5-oxo-5H-benzo[7]annulene-8-carboxylate (18)

Following general method IB, using octyl 3,4,5-trihydroxybenzoate (254 mg, 1.00 mmol) instead of gallic acid, gave 18 as an orange precipitate (205.7 mg, 52.7%): $^1$H NMR (300 MHz, DMSO) δ 14.94 (s, 1H), 9.88 (s, 1H), 9.71 (s, 1H), 8.34 (d, J=1.2 Hz, 1H), 7.57 (d, J=1.5 Hz, 1H), 7.41 (s, 1H), 4.29 (t, J=6.7 Hz, 2H), 4.01 (s, 3H), 1.81-1.64 (m, 2H), 1.45-1.17 (m, 10H), 0.85 (dd, J=8.8, 4.8 Hz, 3H); $^{13}$C NMR (75 MHz, DMSO) δ 183.53, 166.57, 154.15, 152.46, 151.89, 138.46, 138.22, 130.21, 124.13, 116.67, 114.42, 110.42, 66.17, 56.68, 31.67, 29.10, 29.05, 28.56, 25.87, 22.53, 14.40; HRMS (ESI): calcd for: $C_{21}H_{26}O_7$ [M−H]$^−$=389.1606, obsd [M−H]$^−$=389.1605.

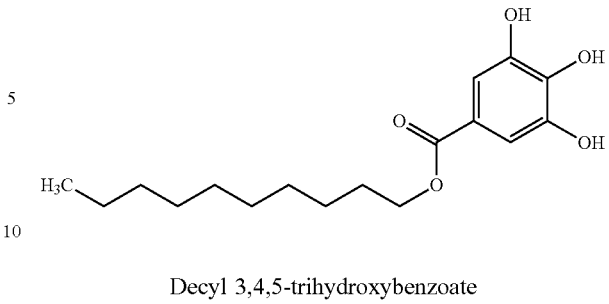

Decyl 3,4,5-trihydroxybenzoate

Following the method used for methyl 3,4,5-trihydroxybenzoate, using 1-decanol (10 mL) instead of MeOH, gave decyl 3,4,5-trihydroxybenzoate as a white solid (743 mg, 48%): $^1$H NMR (400 MHz, DMSO) δ 9.12 (s, 3H), 6.95 (s, 2H), 4.15 (t, J=6.5 Hz, 2H), 1.64 (dd, J=13.9, 6.8 Hz, 2H), 1.40-1.14 (m, 14H), 0.85 (t, J=6.7 Hz, 3H); $^{13}$C NMR (101 MHz, DMSO) δ 166.32, 146.00, 138.80, 120.03, 108.99, 108.92, 64.40, 31.76, 29.45, 29.42, 29.32, 29.16, 28.75, 25.99, 22.56, 14.40.

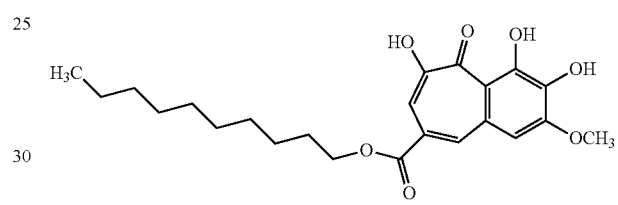

Decyl 3,4,6-trihydroxy-2-methoxy-5-oxo-5H-benzo[7]annulene-8-carboxylate (19)

Following general method IB, using decyl 3,4,5-trihydroxybenzoate (310 mg, 1.00 mmol) instead of gallic acid, gave 19 as an orange precipitate (222 mg, 53%): $^1$H NMR (300 MHz, DMSO) δ 14.96 (s, 1H), 9.76 (s, 2H), 8.34 (s, 1H), 7.57 (s, 1H), 7.42 (s, 1H), 4.29 (t, J=6.6 Hz, 2H), 4.01 (s, 3H), 1.82-1.64 (m, 2H), 1.47-1.14 (m, 14H), 0.83 (t, J=6.6 Hz, 3H); $^{13}$C NMR (75 MHz, DMSO) δ 183.54, 166.58, 154.16, 152.47, 151.90, 138.47, 138.23, 130.22, 124.13, 116.68, 114.43, 110.43, 66.17, 56.68, 31.75, 29.38, 29.14, 29.10, 28.54, 25.85, 22.54, 14.39; HRMS (ESI): calcd for: $C_{23}H_{30}O_7$ [M−H]$^−$=417.1914, obsd [M−H]$^−$=417.1918.

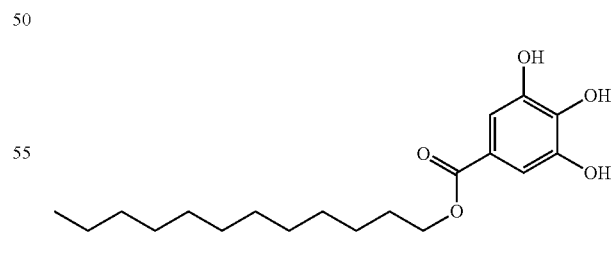

Tetradecyl 3,4,5-trihydroxybenzoate

Following the method used for methyl 3,4,5-trihydroxybenzoate, using 1-tetradecanol (10 g) instead of MeOH, to give tetradecyl 3,4,5-trihydroxybenzoate as a white solid (754.9 mg, 41.2%): $^1$H NMR (300 MHz, Acetone) δ 7.13 (s, 2H), 4.22 (t, J=6.6 Hz, 2H), 1.80-1.65 (m, 2H), 1.54-1.21

(m, 22H), 0.88 (m, 3H); $^{13}$C NMR (75 MHz, Acetone) δ 165.83, 145.10, 137.69, 121.21, 108.83, 99.98, 64.10, 31.73, 25.90, 22.42, 13.45.

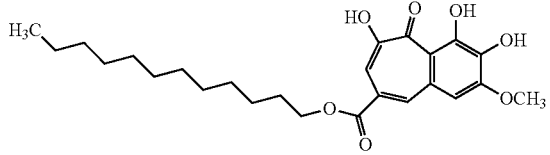 [SMILES: CCCCCCCCCCCCOC(=O)c1cc(O)c(=O)c2c(O)c(O)c(OC)cc2c1]

Tetradecyl 3,4,6-trihydroxy-2-methoxy-5-oxo-5H-benzo[7]annulene-8-carboxylate (20)

Following general method IB, using tetradecyl 3,4,5-trihydroxybenzoate (366.5 mg, 1 mmol) instead of gallic acid, gave 20 as an orange precipitate (195 mg, 41%): $^1$H NMR (300 MHz, DMSO) δ 14.94 (s, 1H), 9.81 (d, 2H), 8.36 (d, J=1.2 Hz, 1H), 7.58 (d, J=1.5 Hz, 1H), 7.43 (s, 1H), 4.30 (t, J=6.6 Hz, 2H), 4.01 (s, 3H), 1.73 (ddd, J=8.3, 6.5, 4.4 Hz, 2H), 1.31-1.15 (m, 22H), 0.84 (dd, J=8.8, 4.7 Hz, 3H); $^{13}$C NMR (75 MHz, DMSO) δ 183.56, 166.61, 154.14, 152.49, 151.89, 138.46, 138.36, 130.17, 124.10, 116.69, 114.46, 110.44, 66.15, 56.68, 31.74, 29.49, 29.45, 29.36, 29.31, 29.15, 29.03, 28.52, 25.82, 22.54, 14.40; HRMS (ESI): calcd for: C$_{27}$H$_{38}$O$_7$ [M–H]$^-$=473.2547, obsd [M–H]$^-$=473.2544.

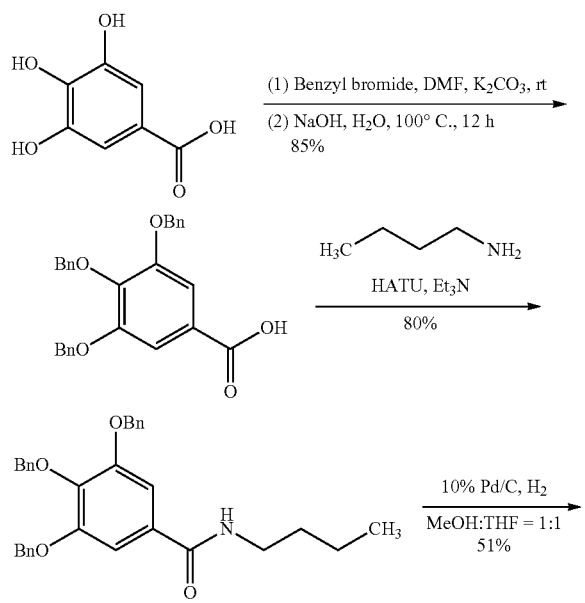

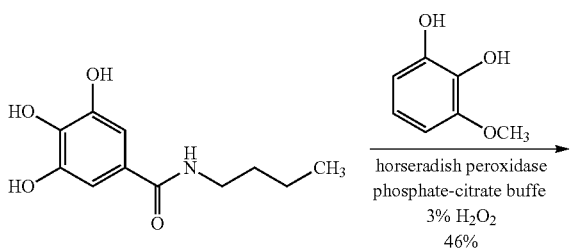

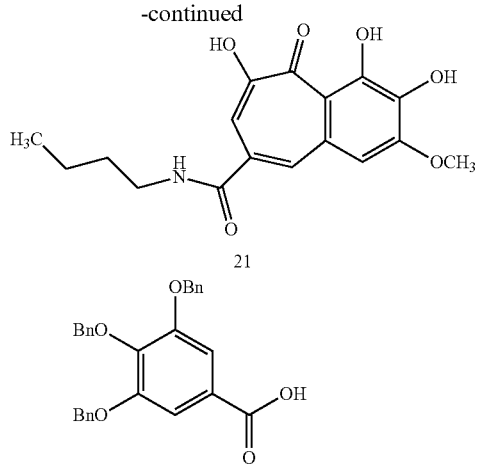

3,4,5-tris(benzyloxy)benzoic acid

Gallic acid (1.70 g, 10.0 mmol) and anhydrous K$_2$CO$_3$ (11.3 g, 82.0 mmol) in DMF (80 mL) was stirred at room temperature for 1 h. BnBr (14.3 mL, 120 mmol) was added dropwise into the solution over 30 min at 40° C. under nitrogen. The reaction mixture was stirred for 12 h at 40° C., then additional H$_2$O (40 mL) and EtOAc (100 mL) were added in the flask. The organic layer was washed with H$_2$O (3×100 mL), dried over anhydrous Na$_2$SO$_4$, filtered and was evaporated to dryness in vacuo. The residue was dissolved in aqueous ethanol (50%, 100 mL) containing 5 M NaOH and refluxed for 12 h. The solution was diluted with H$_2$O (50 mL), adjusted to pH 2 with concentrated HCl and stirred for 30 min at rt. The precipitate was collected and recrystallized from methanol to give colorless needle crystal of 3,4,5-tris(benzyloxy)benzoic acid (3.75 g, 85%): $^1$H NMR (300 MHz, DMSO) δ 12.95 (s, 1H), 7.51-7.26 (m, 17H), 5.19 (s, 4H), 5.05 (s, 2H); $^{13}$C NMR (75 MHz, DMSO) δ 167.29, 152.45, 141.41, 137.83, 137.30, 128.88, 128.65, 128.54, 128.48, 128.35, 128.24, 128.02, 127.06, 126.86, 126.45, 108.64, 74.68, 70.65.

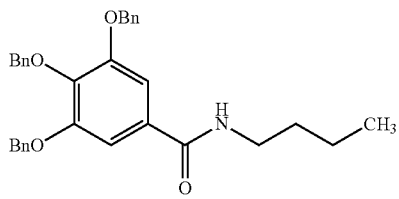 [SMILES: CCCCNC(=O)c1cc(OCc2ccccc2)c(OCc2ccccc2)c(OCc2ccccc2)c1]

3,4,5-tris(benzyloxy)-N-butylbenzamide

To a solution of 3,4,5-tris(benzyloxy)benzoic acid (440 mg, 1 mmol) in dry dichloromethane (5 mL) was added HATU (342 mg, 0.900 mmol), DIPEA (0.35 mL, 2.00 mmol) and 1-butanamine (98 μL, 1.00 mmol). The reaction mixture was stirred at room temperature overnight and the solution was evaporated and purified by flash chromatography on silica gel, using ethyl acetate/hexane (1:6) as eluent, gave 3,4,5-tris(benzyloxy)-N-butylbenzamide as a white solid (398 mg, 80%): $^1$H NMR (300 MHz, Acetone) δ 7.82-7.68 (m, 1H), 7.59-7.19 (m, 17H), 5.18 (s, 4H), 5.09 (s, 2H), 3.38 (td, J=7.1, 5.9 Hz, 2H), 1.67-1.50 (m, 2H), 1.46-1.26 (m, 6H), 0.90 (dd, J=8.3, 5.4 Hz, 3H); $^{13}$C NMR (75 MHz, Acetone) δ 165.64, 152.60, 140.48, 138.08, 137.28, 130.65, 128.39, 128.24, 127.99, 127.82, 127.64, 106.63, 74.56, 70.77, 39.62, 31.45, 29.59, 7.82, 26.55, 22.39, 13.43.

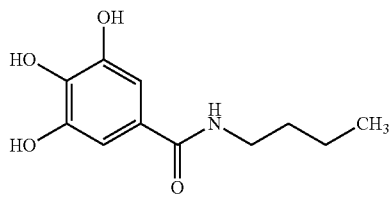 [SMILES: CCCCNC(=O)c1cc(O)c(O)c(O)c1]

N-butyl-3,4,5-trihydroxybenzamide

To a solution of 3,4,5-tris(benzyloxy)-N-butylbenzamide (198 mg, 0.400 mmol) in THF/MeOH (15 mL, 1:1 v/v) was added palladium hydroxide on carbon (palladium 10 wt % on carbon). The suspension was stirred for 13 h at room temperature under a H$_2$ atmosphere. The mixture was filtered through Celite, and the filtrate was concentrated under reduced pressure, using ethyl acetate/hexane (1:4) as eluent, give N-butyl-3,4,5-trihydroxybenzamide as a white solid (46 mg, 51%): $^1$H NMR (300 MHz, Acetone) δ 8.15 (s, 2H), 7.62 (s, 1H), 7.06 (s, 2H), 3.46-3.25 (m, 2H), 1.57 (dq, J=7.5, 6.6 Hz, 2H), 1.43-1.25 (m, 2H), 0.91 (t, J=7.3 Hz, 3H); $^{13}$C NMR (75 MHz, Acetone) δ 167.10, 145.24, 135.96, 125.83, 106.81, 39.35, 31.61, 19.90, 13.24.

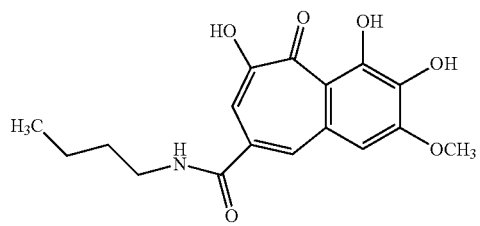 [SMILES: CCCCNC(=O)c1cc(O)c(=O)c2c(O)c(O)c(OC)cc2c1]

N-butyl-3,4,6-trihydroxy-2-methoxy-5-oxo-5H-benzo[7]annulene-8-carboxamide (21)

Following general method IB, using N-butyl-3,4,5-trihydroxybenzamide (113 mg, 0.500 mmol) instead of gallic acid to give 21 as an orange precipitate (78 mg, 46%): $^1$H NMR (300 MHz, DMSO) δ 14.98 (s, 1H), 9.74-9.54 (m, 2H), 8.60 (dd, J=6.6, 2.9 Hz, 1H), 8.02 (s, 1H), 7.47 (s, 1H), 7.29 (s, 1H), 4.00 (s, 3H), 3.26 (dt, J=12.8, 3.5 Hz, 2H), 1.63-1.46 (m, 2H), 1.45-1.05 (m, 78), 0.86 (d, J=6.6 Hz, 3H); $^{13}$C NMR (75 MHz, DMSO) δ 183.10, 167.66, 154.32, 152.60, 151.51, 137.05, 134.78, 131.27, 130.21, 116.56, 115.59, 108.93, 56.50, 31.48, 29.41, 26.64, 22.52, 14.39; HRMS (ESI): calcd for: C$_{19}$H$_{23}$NO$_6$ [M−H]$^-$=360.1454, obsd [M−H]$^-$=360.1452.

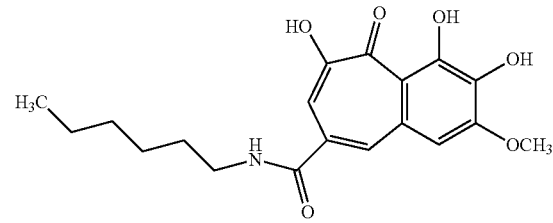 [SMILES: CCCCCCNC(=O)c1cc(O)c(=O)c2c(O)c(O)c(OC)cc2c1]

N-hexyl-3,4,6-trihydroxy-2-methoxy-5-oxo-5H-benzo[7]annulene-8-carboxamide (22)

Following the general method of 21, we get 22 as an orange solid (76 mg, 42%): $^1$H NMR (300 MHz, DMSO) δ 14.98 (s, 1H), 9.74-9.54 (m, 2H), 8.60 (dd, J=6.6, 2.9 Hz, 1H), 8.02 (s, 1H), 7.47 (s, 1H), 7.29 (s, 1H), 4.00 (s, 3H), 3.26 (m, 2H), 1.63-1.46 (m, 2H), 1.45-1.05 (m, 78), 0.86 (d, J=6.6 Hz, 3H); $^{13}$C NMR (75 MHz, DMSO) δ 183.10, 167.66, 154.32, 152.60, 151.51, 137.05, 134.78, 131.27, 130.21, 116.56, 115.59, 108.93, 56.50, 31.48, 29.41, 26.64, 22.52, 14.39; HRMS (ESI): calcd for: C$_{19}$H$_{23}$NO$_6$ [M−H]$^-$=360.1454, obsd [M−H]$^-$=360.1452.

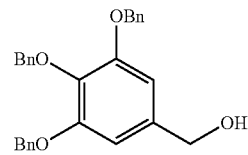 [SMILES: OCc1cc(OCc2ccccc2)c(OCc2ccccc2)c(OCc2ccccc2)c1]

3,4,5-tris(benzyloxy)phenyl)methanol

A solution of benzyl 3,4,5-tris(benzyloxy)benzoate (1.06 g, 2.00 mmol) in THY (10 mL) was added to a stiffed suspension of lithium aluminium hydride (379 mg, 8.00 mmol) in THF (15 mL) at 0° C. over 1 hr. The mixture was then stirred at room temperature for 12 h and subsequently cooled to 0° C. before slowing addition of water (40 mL). The mixture was extracted with EtOAc (3×20 mL). The organic extracts were dried with Na$_2$SO$_4$ and concentrated under reduced pressure. Purified by flash chromatography on silica gel, using ethyl acetate/hexane (1:2) as eluent, gave 3,4,5-tris(benzyloxy)phenyl)methanol as a colorless oil (505 mg, 59%): $^1$H NMR (300 MHz, Acetonitrile) δ 7.55-7.20 (m, 15H), 6.73 (s, 2H), 5.10 (s, 4H), 4.97 (s, 2H), 4.48 (d, J=5.8 Hz, 2H), 3.19 (t, J=5.9 Hz, 1H); $^{13}$C NMR (75 MHz, Acetonitrile) δ 153.88, 139.41, 139.37, 138.70, 129.73, 129.63, 129.39, 129.17, 129.04, 106.77, 75.85, 71.83, 64.93.

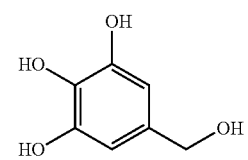 [SMILES: OCc1cc(O)c(O)c(O)c1]

5-(hydroxymethyl)benzene-1,2,3-triol

To a solution of 3,4,5-tris(benzyloxy)phenyl)methanol (171 mg, 0.401 mmol) in THF/MeOH (15 mL, 1:1 v/v) was added palladium hydroxide on carbon (palladium 10 wt % on carbon). The suspension was stirred for 13 h at room temperature under a H$_2$ atmosphere. The mixture was filtered through Celite, and the filtrate was evaporated and purified by flash chromatography on silica gel, using ethyl acetate/hexane (1:2) as eluent, give 5-(hydroxymethyl)benzene-1,2,3-triol as a colorless oil (33 mg, 53%): $^1$H NMR (300 MHz, Acetone) δ 7.58 (s, 2H), 6.42 (s, 2H), 4.42 (s, 2H); $^{13}$C NMR (75 MHz, Acetone) δ 145.50, 133.52, 131.60, 106.29, 106.24, 105.86, 63.94.

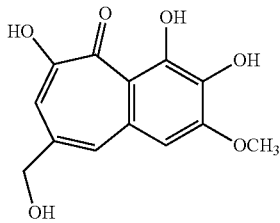 [SMILES: COc1cc2cc(CO)cc(O)c(=O)c2c(O)c1O]

3,4,6-trihydroxy-8-(hydroxymethyl)-2-methoxy-5H-benzo[7]annulen-5-one (23)

Following general method IB, using 5-(hydroxymethyl)benzene-1,2,3-triol (78 mg, 0.500 mmol) instead of gallic acid, gave 23 as an orange precipitate (68 mg, 52%): $^1$H NMR (300 MHz, DMSO) δ 15.05 (s, 1H), 9.47 (s, 1H), 9.29 (s, 1H), 7.54 (s, 1H), 7.18-6.98 (m, 2H), 5.53 (dd, J=7.4, 4.0 Hz, 1H), 4.43 (d, J=5.0 Hz, 2H), 3.96 (s, 3H); $^{13}$C NMR (75 MHz, DMSO) δ 182.50, 154.53, 152.95, 151.15, 137.75, 135.25, 133.02, 131.39, 117.59, 116.16, 106.91, 66.10, 56.37; HRMS (ESI): calcd for: C$_{13}$H$_{12}$O$_6$ [M−H]$^−$=263.0558, obsd [M−H]$^−$=263.0561.

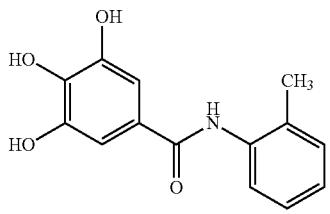 [SMILES: Cc1ccccc1NC(=O)c1cc(O)c(O)c(O)c1]

3,4,5-trihydroxy-N-o-tolylbenzamide

Following general synthesize method of N-butyl-3,4,5-trihydroxybenzamide, using o-toluidine (160 pt, 1.00 mmol) instead of 1-butanamine, gave an oil mixture. This was purified by flash chromatography on silica gel. Using ethyl acetate/hexane (1:4) as eluent, gave 3,4,5-trihydroxy-N-o-tolylbenzamide as a colorless oil (203.77 mg, 78.6%): $^1$H NMR (300 MHz, Acetone) δ 8.77 (s, 1H), 8.18 (s, 2H), 7.66-7.56 (m, 1H), 7.28-7.02 (m, 5H), 2.33 (s, 3H); $^{13}$C NMR (75 MHz, Acetone) δ 165.28, 145.31, 136.90, 136.36, 132.12, 130.23, 125.99, 125.92, 125.20, 125.17, 125.05, 124.93, 107.07, 17.31.

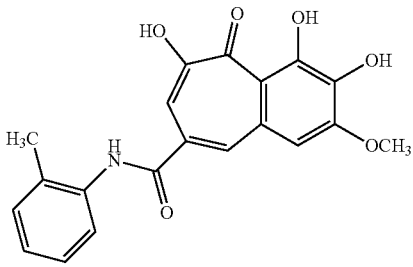 [SMILES: COc1cc2cc(C(=O)Nc3ccccc3C)cc(O)c(=O)c2c(O)c1O]

3,4,6-trihydroxy-2-methoxy-5-oxo-N-o-tolyl-5H-benzo[7]annulene-8-carboxamide (24)

Following general method IB, using 3,4,5-trihydroxy-N-o-tolylbenzamide (128 mg, 0.500 mmol) instead of gallic acid to give 24 as an orange precipitate (85 mg, 45%): $^1$H NMR (300 MHz, DMSO) δ 15.00 (s, 1H), 10.07 (s, 1H), 9.73 (d, 2H), 8.20 (d, J=1.1 Hz, 1H), 7.54 (d, J=1.4 Hz, 1H), 7.42-7.10 (m, 5H), 4.01 (s, 3H), 2.27 (s, 3H); $^{13}$C NMR (75 MHz, DMSO) δ 183.28, 167.13, 154.44, 152.62, 151.62, 137.27, 136.88, 135.43, 134.06, 131.15, 130.85, 130.16, 126.76, 126.51, 116.63, 115.61, 109.23, 56.55, 18.46; FIRMS (ESI): calcd for: C$_{20}$H$_{17}$NO$_6$ [M−H]$^−$=366.0984, obsd [M−H]$^−$=366.0982.

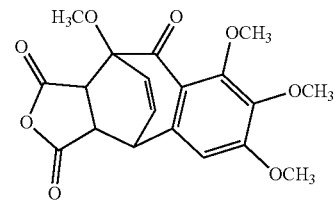 [SMILES: COc1cc2c(c(OC)c1OC)C(=O)C1(OC)C=CC2C2C(=O)OC(=O)C21]

25 Following general method II, gave 25 as a white solid (28 mg, 75%): $^1$H NMR (300 MHz, CDCl$_3$) δ 6.65-6.56 (m, 2H), 6.16 (d, J=9.2 Hz, 1H), 4.16 (dd, J=7.2, 2.6 Hz, 1H), 3.98 (d, J=0.8 Hz, 1H), 3.95 (s, 3H), 3.91 (s, 3H), 3.84 (s, 3H), 3.74 (dd, J=9.3, 2.4 Hz, 1H), 3.66 (s, 3H); $^{13}$C NMR (75 MHz, CDCl$_3$) δ 188.17, 171.15, 166.70, 157.30, 156.93, 143.10, 139.31, 133.82, 132.62, 119.40, 106.62, 85.23, 61.98, 60.95, 56.22, 54.20, 48.24, 44.61, 44.56; HRMS (ESI): calcd for: C$_{19}$H$_{18}$O$_8$ [M+H]$^+$=375.1066, obsd [M+H] r=375.1075.

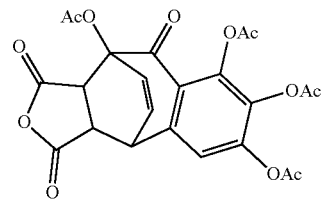 [SMILES: CC(=O)Oc1cc2c(c(OC(C)=O)c1OC(C)=O)C(=O)C1(OC(C)=O)C=CC2C2C(=O)OC(=O)C21]

26 Following general method II, using 9 (39 mg, 0.100 mmol) instead of 6 to give 26 as an white solid (25 mg, 52%): $^1$H NMR (300 MHz, CDCl$_3$) δ 7.26 (s, 1H), 6.81-6.70 (m, 1H), 6.21-6.09 (m, 1H), 4.92-4.71 (m, 1H), 4.40-4.23 (m, 1H), 3.86 (d, J=6.0, 2.0, Hz, 1H), 2.313-2.29 (m, 12H); $^{13}$C NMR (101 MHz, DMSO) δ 171.67, 169.16, 168.10, 167.91, 167.64, 167.28, 146.85, 146.09, 141.54, 136.36, 132.30, 122.26, 121.96, 121.85, 83.30, 48.51, 43.75, 42.55, 21.26, 20.79, 20.53, 20.19; HRMS (ESI): calcd for: $C_{23}H_{18}O_{12}$ [M+Na]$^+$=509.0678, obsd [M+Na]$^+$=509.0691.

Biological Testing

In vitro testing was conducted using primary cells (isolated microglial cells) incubated with Pam3CSK4 and CU-CPT22 for 2 hours. FIG. 9 shows the dose-dependent inhibition of IL-1β by CU-CPT22 in these primary cells.

In vivo testing was conducted by the administration of Pam3CSK4 and CU-CPTP22. CU-CPT22 (5 ng or 50 ng), suspended in 5 µl sterile saline or vehicle, was co-administered with the TLR2 agonist Pam3CSK4 (40 ng/4 µl) to the animal via the cisterna magna (ICM) with a 1 µl air bubble separating the two reagents. Two hours after injection, the animal's hippocampus was collected for pro-inflammatory mRNA analysis using real time RT-PCR procedures. The data demonstrate that CU-CPT22 strongly inhibits IL-1β mRNA expression (FIG. 10*a*), TNF-α mRNA expression (FIG. 10*b*) and M-6 mRNA expression (FIG. 10*c*) in vivo. (N=8 for each group).

The foregoing discussion of the disclosure has been presented for purposes of illustration and description and is not intended to limit the disclosure to the forms disclosed herein. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound having the chemical structure:

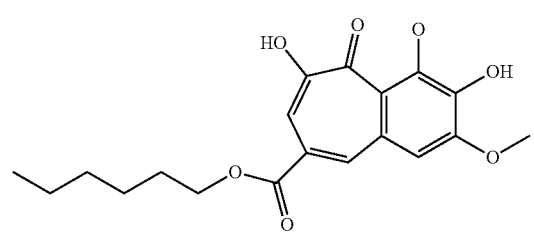 [SMILES: CCCCCCOC(=O)c1cc(O)c(=O)c2c(O)c(O)c(OC)cc2c1]

or a pharmaceutically acceptable salt thereof.

2. A compound having the chemical structure:

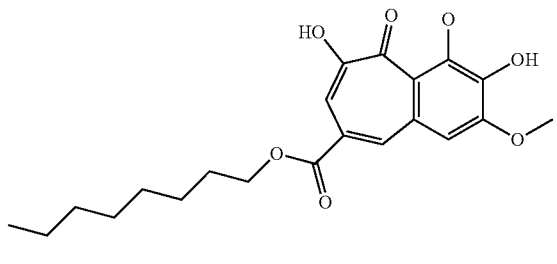 [SMILES: CCCCCCCCOC(=O)c1cc(O)c(=O)c2c(O)c(O)c(OC)cc2c1]

or a pharmaceutically acceptable salt thereof.

3. A compound having the chemical structure:

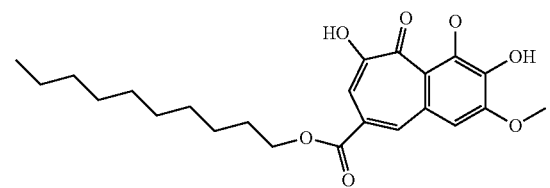 [SMILES: CCCCCCCCCCOC(=O)c1cc(O)c(=O)c2c(O)c(O)c(OC)cc2c1]

or a pharmaceutically acceptable salt thereof.

4. A compound having the chemical structure:

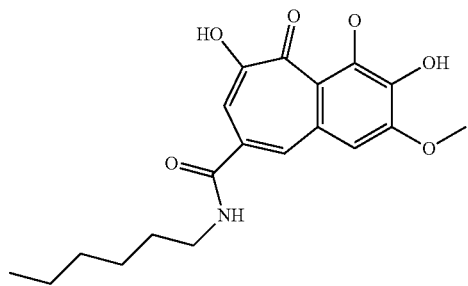 [SMILES: CCCCCCNC(=O)c1cc(O)c(=O)c2c(O)c(O)c(OC)cc2c1]

or a pharmaceutically acceptable salt thereof.

5. A compound having the chemical structure:

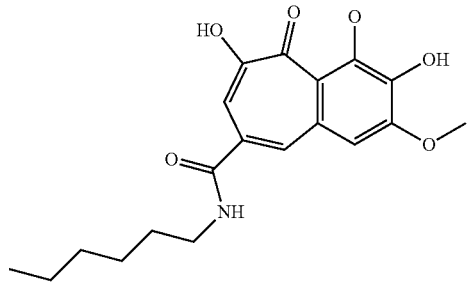 [SMILES: CCCCCCNC(=O)c1cc(O)c(=O)c2c(O)c(O)c(OC)cc2c1]

or a pharmaceutically acceptable salt thereof.

6. A compound having the chemical structure:

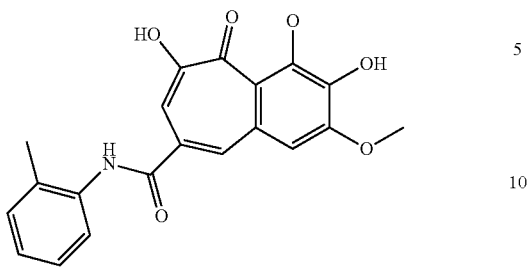

or a pharmaceutically acceptable salt thereof.

7. A pharmaceutical composition comprising a compound of claims 1, 2, 3, 4, 5, or 6, or a salt thereof, and a pharmaceutically acceptable excipient.

8. A method for treating a clinical condition associated with signaling mediated by TLR1/2 comprising administering to a subject in need of such a treatment a therapeutically effective amount of a compound of any one of claims 1-6, wherein the clinical condition is psoriasis or acne vulgaris.

* * * * *

UNITED STATES PATENT AND TRADEMARK OFFICE
CERTIFICATE OF CORRECTION

PATENT NO. : 9,517,993 B2
APPLICATION NO. : 14/417676
DATED : December 13, 2016
INVENTOR(S) : Hang Yin et al.

Page 1 of 3

It is certified that error appears in the above-identified patent and that said Letters Patent is hereby corrected as shown below:

In Column 41, Line 60, please delete chemical structure " 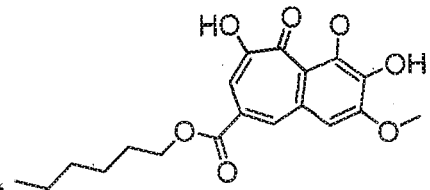 " and insert chemical structure -- 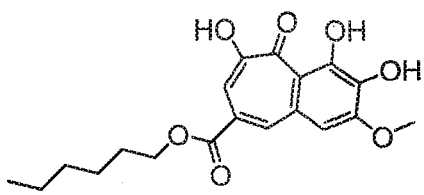 --

In Column 42, Line 10, please delete chemical structure " 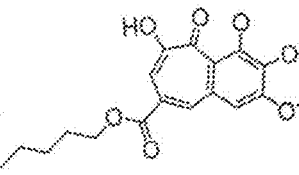 " and insert chemical structure -- 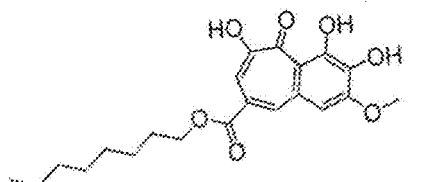 --

Signed and Sealed this
Third Day of July, 2018

Andrei Iancu
*Director of the United States Patent and Trademark Office*

CERTIFICATE OF CORRECTION (continued)
U.S. Pat. No. 9,517,993 B2

In Column 42, Line 25, please delete chemical structure " 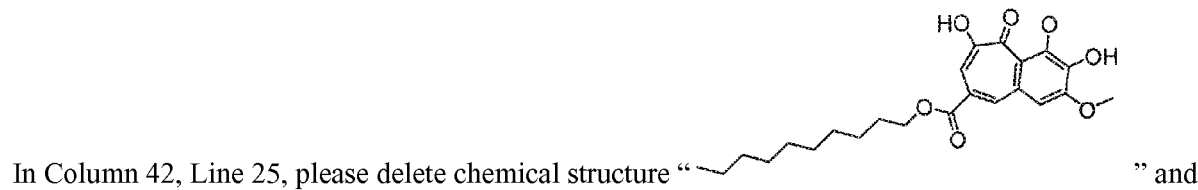 " and insert chemical structure -- 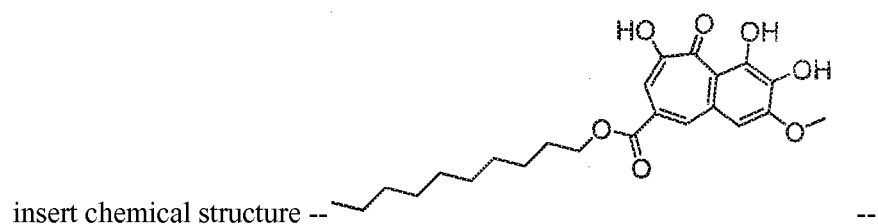 --

In Column 42, Line 40, please delete chemical structure " 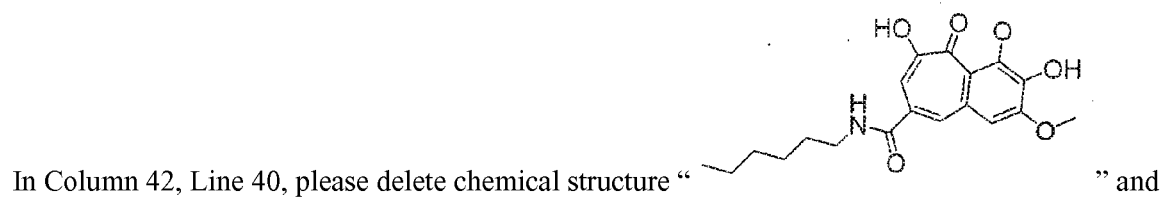 " and insert chemical structure --  --

In Column 42, Line 60, please delete chemical structure " 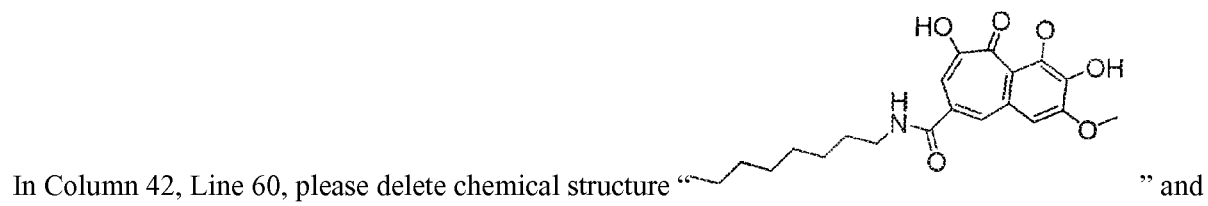 " and insert chemical structure -- 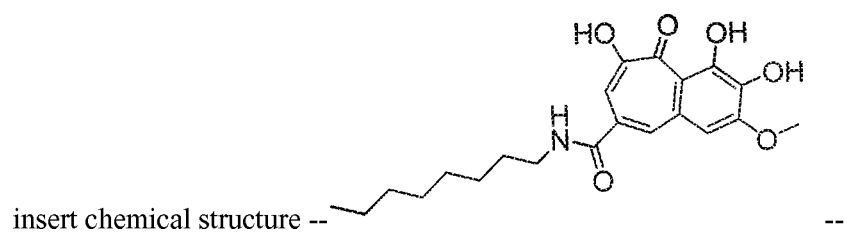 --

CERTIFICATE OF CORRECTION (continued)
U.S. Pat. No. 9,517,993 B2

In Column 43, Line 10, please delete chemical structure " 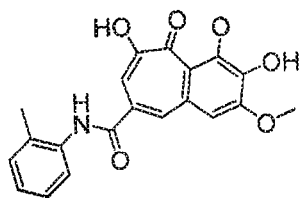 " and insert chemical structure -- 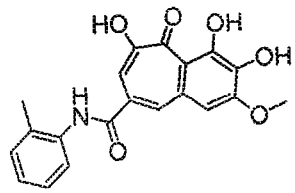 --